United States Patent
Karlsson et al.

(10) Patent No.: US 11,466,329 B2
(45) Date of Patent: Oct. 11, 2022

(54) DETECTION OF BLA$_{IMP}$ ANTIBACTERIAL RESISTANCE GENES

(71) Applicant: The United States of America as represented by the Department of Health and Human Services, Bethesda, MD (US)

(72) Inventors: Linda Maria Erika Karlsson, Atlanta, GA (US); Davina Elaine Campbell, Decatur, GA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 378 days.

(21) Appl. No.: 16/615,725

(22) PCT Filed: Jun. 13, 2018

(86) PCT No.: PCT/US2018/037395
§ 371 (c)(1),
(2) Date: Nov. 21, 2019

(87) PCT Pub. No.: WO2018/232028
PCT Pub. Date: Dec. 20, 2018

(65) Prior Publication Data
US 2020/0172962 A1    Jun. 4, 2020

Related U.S. Application Data

(60) Provisional application No. 62/519,663, filed on Jun. 14, 2017.

(51) Int. Cl.
*C12Q 1/689* (2018.01)
*C12Q 1/6806* (2018.01)
*G01N 21/64* (2006.01)

(52) U.S. Cl.
CPC ........... *C12Q 1/689* (2013.01); *C12Q 1/6806* (2013.01); *G01N 21/6428* (2013.01); *C12Q 2600/106* (2013.01); *G01N 2021/6439* (2013.01)

(58) Field of Classification Search
CPC .......... C12Q 1/68; C12Q 1/689; C07H 21/00; C12P 19/34
See application file for complete search history.

(56) References Cited

U.S. PATENT DOCUMENTS

| 8,324,364 B2 | 12/2012 | Whiteford et al. | |
| 2003/0124545 A1* | 7/2003 | Rothman | C12Q 1/689 |
| | | | 435/6.15 |
| 2009/0163382 A1* | 6/2009 | Oh | C12Q 1/689 |
| | | | 506/17 |
| 2011/0091886 A1* | 4/2011 | Hirama | C12Q 1/689 |
| | | | 435/6.16 |

FOREIGN PATENT DOCUMENTS

| CN | 102534013 B | * | 9/2013 |
| WO | WO 2010/130882 A1 | | 11/2010 |
| WO | WO 2016/094607 A2 | | 6/2016 |

OTHER PUBLICATIONS

Amudhan et al., J. of InfectionDev Countries 6(11) : 757 (Year: 2012).*
Chao et al., Intl. J. of Antimicrobial Agents32 : 363 (Year: 2008).*
Conejo et al., J. of Microbial Chemotherapy (Year: 2010).*
EU176818 (Year: 2008).*
Livak et al. PCR Methods and Applications4:357 (Year: 1995).*
Mendes et al. Antimicrobial Agents and Chemotherapy52(2) : 798 (Year: 2008).*
Accession No. AWC87235, XP055499671, Bacterial IMP gene, SEQ ID 164, Sep. 29, 2006.
Accession No. AZU70749, XP055499670, Bacterial IMP1 gene targeting oligonucleotide probe #90, May 24, 2012.
Campbell et al., "Development of a Multiplex TaqMan Probe-Based Real-Time PCR Assay for Detection of blaIMP Variants," Poster Presentation, ASM Microbe, New Orleans, LA, Jun. 2, 2017.
Ellington et al., "Multiplex PCR for rapid detection of genes encoding acquired metallo-β-lactamases," *J Antimicrob Chemother.* 59:321-322, 2006.
Mendes et al.., "Rapid Detection and Identification of Metallo-β-Lactamase-Encoding Genes by Multiplex Real-Time PCR Assay and Melt Curve Analysis," *J Clin Microbiol.* 45:544-547, 2007.
Queenan & Bush, "Carbapenemases: the Versatile β-Lactamases," *Clin Microbiol Rev.* 20:440-458, 2007.
van der Zee et al., "Multi-centre evaluation of real-time multiplex PCR for detection of carbapenemase genes OXA-48, VIM, IMP, NDM and KPC," *BMC Infect Dis.* 14:27, 2014.
van der Zee et al., Supplementary Material for XP055499666, Jan. 14, 2014.
Watanabe et al.., "Transferable Imipenem Resistance in *Pseudomonas aeruginosa,"* Antimicrob Agents Chemother. 35:147-151, 1991.
International Search Report and Written Opinion dated Sep. 3, 2018 for International Application No. PCT/US2018/037395 (16 pages).

* cited by examiner

*Primary Examiner* — Ethan C Whisenant
(74) *Attorney, Agent, or Firm* — Klarquist Sparkman, LLP

(57) ABSTRACT

Methods and compositions are provided for the detection of BlaIMP. The disclosed methods and compositions can detect all known IMP variants in a single, rapid assay.

20 Claims, 2 Drawing Sheets
Specification includes a Sequence Listing.

SEQUENCE LISTING

```
<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: IMP Forward Primer
<220> FEATURE:
<221> NAME/KEY: misc_feature
<222> LOCATION: (6)..(6)
<223> OTHER INFORMATION: locked nucleic acid

<400> SEQUENCE: 1
ggcggaatag agtggct                                                    17

<210> SEQ ID NO 2
<211> LENGTH: 27
<212> TYPE: DNA
<213> ORGANISM: Artificial Sequence
<220> FEATURE:
<223> OTHER INFORMATION: IMP Reverse Primer
<220> FEATURE:
<221> NAME/KEY: misc_feature
<222> LOCATION: (10)..(10)
<223> OTHER INFORMATION: H = Mixture of A, C, and T at this position,
      not necessarily equimolar
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (20)..(20)
<223> OTHER INFORMATION: M is a mixture of A and C at this position, not
      necessarily equimolar
<220> FEATURE:
<221> NAME/KEY: misc_feature
<222> LOCATION: (23)..(23)
<223> OTHER INFORMATION: B is a mixture of C, G, and T at this position,
      not necessarily equimolar

<400> SEQUENCE: 2
ccttaccgth tttttnaagm agbtcat                                         27

<210> SEQ ID NO 3
<211> LENGTH: 26
<212> TYPE: DNA
<213> ORGANISM: Artificial Sequence
<220> FEATURE:
<223> OTHER INFORMATION: IMP Reverse Primer

<400> SEQUENCE: 3
tttgtagctt gcaccttatt gtcttt                                          26

<210> SEQ ID NO 4
<211> LENGTH: 25
<212> TYPE: DNA
<213> ORGANISM: Artificial Sequence
<220> FEATURE:
<223> OTHER INFORMATION: IMP Probe
<220> FEATURE:
<221> NAME/KEY: misc_feature
<222> LOCATION: (2)..(2)
<223> OTHER INFORMATION: Y = Mixture of C and T at this position, not
      necessarily equimolar
```

```
<220> FEATURE:
<221> NAME/KEY: misc_feature
<222> LOCATION: (7)..(8)
<223> OTHER INFORMATION: R = Mixture of A and G at this position, not
      necessarily equimolar
<220> FEATURE:
<221> NAME/KEY: misc_feature
<222> LOCATION: (11)..(11)
<223> OTHER INFORMATION: H=Mixture of A, C, and T at this position, not
      necessarily equimolar
<220> FEATURE:
<221> NAME/KEY: misc_feature
<222> LOCATION: (12)..(12)
<223> OTHER INFORMATION: Locked nucleic acid at this position
<220> FEATURE:
<221> NAME/KEY: misc_feature
<222> LOCATION: (14)..(15)
<223> OTHER INFORMATION: Y=Mixture of C and T at this position, not
      necessarily equimolar
<220> FEATURE:
<221> NAME/KEY: misc_feature
<222> LOCATION: (17)..(17)
<223> OTHER INFORMATION: M= Mixture of A and C at this position, not
      necessarily equimolar
<220> FEATURE:
<221> NAME/KEY: misc_feature
<222> LOCATION: (18)..(18)
<223> OTHER INFORMATION: Locked nucleic acid at this position
<220> FEATURE:
<221> NAME/KEY: misc_feature
<222> LOCATION: (20)..(20)
<223> OTHER INFORMATION: R = Mixture of A and G at this position, not
      necessarily equimolar
<220> FEATURE:
<221> NAME/KEY: misc_feature
<222> LOCATION: (22)..(22)
<223> OTHER INFORMATION: Locked nucleic acid at this position

<400> SEQUENCE: 4
aytctcrrtc hatyycmacr tatgc                                           25

<210> SEQ ID NO 5
<211> LENGTH: 23
<212> TYPE: DNA
<213> ORGANISM: Artificial Sequence
<220> FEATURE:
<223> OTHER INFORMATION: IMP probe
<220> FEATURE:
<221> NAME/KEY: misc_feature
<222> LOCATION: (4)..(4)
<223> OTHER INFORMATION: Locked nucliec acid at this position
<220> FEATURE:
<221> NAME/KEY: misc_feature
<222> LOCATION: (10)..(10)
<223> OTHER INFORMATION: Locked nucliec acid at this position
<220> FEATURE:
<221> NAME/KEY: misc_feature
<222> LOCATION: (14)..(14)
<223> OTHER INFORMATION: Locked nucliec acid at this position
<220> FEATURE:
<221> NAME/KEY: misc_feature
<222> LOCATION: (17)..(17)
<223> OTHER INFORMATION: Locked nucliec acid at this position
<220> FEATURE:
<221> NAME/KEY: misc_feature
<222> LOCATION: (22)..(22)
<223> OTHER INFORMATION: Locked nucliec acid at this position

<400> SEQUENCE: 5
tatgcatctg aattaacaaa tga                                             23

<210> SEQ ID NO 6
<211> LENGTH: 22
<212> TYPE: DNA
<213> ORGANISM: Artificial Sequence
```

```
<220> FEATURE:
<223> OTHER INFORMATION: 16S rRNA-Forward Primer

<400> SEQUENCE: 6
tggagcatgt ggtttaattc ga                                            22

<210> SEQ ID NO 7
<211> LENGTH: 19
<212> TYPE: DNA
<213> ORGANISM: Artificial Sequence
<220> FEATURE:
<223> OTHER INFORMATION: 16S rRNA-reverse primer

<400> SEQUENCE: 7
tgcgggactt aacccaaca                                                19

<210> SEQ ID NO 8
<211> LENGTH: 23
<212> TYPE: DNA
<213> ORGANISM: Artificial Sequence
<220> FEATURE:
<223> OTHER INFORMATION: 16S rRNA-Probe
<220> FEATURE:
<221> NAME/KEY: misc_feature
<222> LOCATION: (16)..(16)
<223> OTHER INFORMATION: R = Mixture of A and G at this position, not
      necessarily equimolar

<400> SEQUENCE: 8
cacgagctga cgacarccat gca                                           23
```

DETECTION OF BLA$_{IMP}$ ANTIBACTERIAL RESISTANCE GENES

CROSS-REFERENCE TO RELATED APPLICATION

This is the U.S. National Stage of International Application No. PCT/US2018/037395, filed Jun. 13, 2018, which was published in English under PCT Article 21(2), which in turn claims the benefit of U.S. Provisional Application No. 62/519,663 filed Jun. 14, 2017. The provisional application is incorporated herein in its entirety.

FIELD

This disclosure relates to probes and primers for detecting antimicrobial resistance genes (such as a bla$_{IMP}$ allele that encodes an imipenemase (IMP)), kits that include such probes and primers, and methods of using the probes and primers.

BACKGROUND

Imipenemase (IMP) metallo-β-lactamases (MBL) hydrolyze clinically important β-lactam antibiotics including carbapenems, cephalosporins, and penicillins. Currently, 74 bla$_{IMP}$ variants sharing about 80-99.6% amino acid identity have been reported. The bla$_{IMP}$ genes are generally found on plasmids making them highly mobile and a serious public health concern.

Phenotypic testing methods (e.g., broth microdilution, MBL disk detection kits, and Etest MBL strips) to identify carbapenemase-producing isolates can be difficult to interpret, time consuming, and cannot identify specific resistance mechanisms.

As such, there is a need in the art for a rapid test for bla$_{IMP}$ to readily detect a broad array of IMP variants to direct clinical use of impacted classes of antibiotics.

SUMMARY

The present disclosure provides an isolated probe including or consisting of the nucleic acid sequence of SEQ ID NO: 4 and at least one attached detectable label. In some embodiments, the at least one attached detectable label is a radioactive isotope, enzyme substrate, co-factor, ligand, chemiluminescent agent, fluorophore, hapten, enzyme, chemical, fluorescence quencher, or a combination thereof. In some embodiments, the at least one attached detectable label is a fluorophore, fluorescence quencher, or both.

In another aspect, the disclosure provides an isolated primer including or consisting of the nucleic acid sequence of SEQ ID NO: 1 or SEQ ID NO: 2.

The disclosure also provides a set of nucleic acid molecules, such as (i) a detectably labeled probe including or consisting of the nucleic acid sequence of SEQ ID NO: 5, a detectably labeled probe including or consisting of the nucleic acid sequence of SEQ ID NO: 4, or both probes; (ii) a forward primer including or consisting of the nucleic acid sequence of SEQ ID NO: 1; and (iii) one or more reverse primers including or consisting of the nucleic acid sequence of SEQ ID NO: 2, SEQ ID NO: 3, or both SEQ ID NO: 2 and SEQ ID NO: 3. In some embodiments, each probe in the set of nucleic acid molecules is labeled with a radioactive isotope, enzyme substrate, co-factor, ligand, chemiluminescent agent, fluorophore, hapten, enzyme, chemical, fluorescence quencher, or combination thereof. In some embodiments, each probe is labeled with a fluorophore. In some embodiments, each probe is labeled with one or more fluorescence quenchers. In some embodiments, each probe (e.g., SEQ ID NO: 4 and SEQ ID NO: 5) is labeled with one or more a fluorophores and one or more fluorescence quenchers. In some embodiments, each probe (e.g., SEQ ID NO: 4 and SEQ ID NO: 5) in the set of nucleic acid molecules is labeled with a different fluorophore, for example at the 5'-end of the probe. In some embodiments, each probe (e.g., SEQ ID NO: 4 and SEQ ID NO: 5) in the set of nucleic acid molecules is labeled with a different fluorophore (e.g., at the 5'-end of the probe), and a fluorescence quencher (e.g., at the 3-end of the probe), wherein the fluorescence quencher can be the same or different between probes.

The disclosure provides a kit for detecting a bla$_{IMP}$ allele in a sample. The kit can include: (i) a detectably labeled probe including or consisting of the nucleic acid sequence of SEQ ID NO: 4, a detectably labeled probe including or consisting of the nucleic acid sequence of SEQ ID NO: 5, or both probes; (ii) a forward primer including or consisting of the nucleic acid sequence of SEQ ID NO: 1; (iii) one or more reverse primers including or consisting of the sequence shown in SEQ ID NO: 2, SEQ ID NO: 3, or both SEQ ID NO: 2 and SEQ ID NO: 3; and (iv) one or more reagents for PCR, such as a one or more of a polymerase (such as a DNA polymerase), dNTPs, and MgCl$_2$. In some embodiments, each probe in the kit is labeled (e.g., has attached thereto, such as a covalent attachment) with a radioactive isotope, enzyme substrate, co-factor, ligand, chemiluminescent agent, fluorophore, hapten, enzyme, chemical, fluorescence quencher, or combination thereof. In some embodiments, each probe is labeled with a fluorophore. In some embodiments, each probe in the kit is labeled with one or more fluorescence quenchers. In some embodiments, each probe (e.g., SEQ ID NO: 4 and SEQ ID NO: 5) in the kit is labeled with one or more a fluorophores and one or more fluorescence quenchers. In some embodiments, each probe (e.g., SEQ ID NO: 4 and SEQ ID NO: 5) in the kit is labeled with a different fluorophore, for example at the 5'-end of the probe. In some embodiments, each probe (e.g., SEQ ID NO: 4 and SEQ ID NO: 5) in the kit is labeled with a different fluorophore (e.g., at the 5'-end of the probe), and a fluorescence quencher (e.g., at the 3-end of the probe), wherein the fluorescence quencher can be the same or different between probes.

Methods of detecting a bla$_{IMP}$ allele in a sample are provided. The method can include contacting the sample with one or more detectably labeled nucleic acid probes including or consisting of the nucleic acid sequence of SEQ ID NO: 4, SEQ ID NO 5, or both SEQ ID NO: 4 and SEQ ID NO: 5; detecting or measuring hybridization between the one or more detectably labeled probes and the bla$_{IMP}$ allele, wherein detection of hybridization indicates a bla$_{IMP}$ allele is present in the sample. In another aspect, the disclosure provides the use of a detectably labeled probe including or consisting of the sequence shown in SEQ ID NO: 4, SEQ ID NO: 5, or both SEQ ID NO: 4 and SEQ ID NO: 5; a forward primer including or consisting of the sequence shown in SEQ ID NO: 1; and one or more reverse primers including or consisting of the sequence shown in SEQ ID NO: 2, SEQ ID NO: 3, or both SEQ ID NO: 2 and SEQ ID NO: 3 for detecting one or more bla$_{IMP}$ alleles in a sample. In some embodiments, the bla$_{IMP}$ allele encodes an imipenemase (IMP). In some embodiments, the IMP is one or more of IMP-1, IMP-2, IMP-3, IMP-4, IMP-5, IMP-6, IMP-7, IMP-8, IMP-9, IMP10, IMP-11, IMP-12, IMP-13, IMP-14, IMP- 15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, IMP-75, and variants thereof. In some embodiments, the IMP is one or more of IMP-1, IMP-4, IMP-27, IMP-14, IMP-18, IMP-26, IMP-27, and variants thereof.

In some embodiments, the one or more detectably labeled probes used in such a method are each labeled with a radioactive isotope, enzyme substrate, co-factor, ligand, chemiluminescent agent, fluorophore, hapten, enzyme, chemical, fluorescence quencher, or combination thereof. In some embodiments, the fluorophore is fluorescein (FAM) or 6-hexachloro-fluorescein (HEX). In some embodiments, the probe used in the method is labeled with a fluorophore, fluorescence quencher, or both. In some embodiments, the fluorescence quencher is a dark quencher, such as BHQ® dye (2,5-Di-(t-butyl)-1,4-hydroquinone). In some embodiments, each probe used in the method is detectably labeled with a different label, for example which emit a different detectable signal. For example, each probe used (e.g., SEQ ID NO: 4 and SEQ ID NO: 5) can be labeled with one or more a fluorophores and one or more fluorescence quenchers. In some embodiments, each probe used (e.g., SEQ ID NO: 4 and SEQ ID NO: 5) is labeled with a different fluorophore, for example at the 5'-end of the probe. In some embodiments, each probe used (e.g., SEQ ID NO: 4 and SEQ ID NO: 5) is labeled with a different fluorophore (e.g., at the 5'-end of the probe), and a fluorescence quencher (e.g., at the 3-end of the probe), wherein the fluorescence quencher can be the same or different between probes.

The sample can include a bacterial isolate. In some embodiments, the sample is a biological sample from a subject known or suspected of having a bacterial infection. In some embodiments, the sample includes blood, derivatives of blood, fractions of blood, serum, extracted galls, biopsied or surgically removed tissue, unfixed tissue, frozen tissue, formalin-fixed tissue, paraffin-embedded tissue, autopsy sample, tears, milk, skin scrapes, surface washings, urine, sputum, cerebrospinal fluid, prostate fluid, pus, bone marrow aspirates, middle ear fluids, tracheal aspirates, nasopharyngeal aspirates or swabs, nasal swabs, nasal washes, throat swabs, dual nasopharyngeal/throat swabs, lower respiratory tract specimens, bronchoalveolar lavage, bronchial wash, sputum, lung tissue, oropharyngeal aspirates or swabs, saliva, rectal swab, vaginal swab or tissue, or bacterial culture. In some embodiments, the sample is an environmental or food sample suspected of bacterial contamination.

The method can further include amplifying nucleic acid molecules in the sample (such as one or more IMP nucleic acid molecules, such as one or more of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75) with a forward primer comprising or consisting of the nucleic acid sequence of SEQ ID NO: 1 and a reverse primer comprising or consisting of the nucleic acid sequence of SEQ ID NO: 2, SEQ ID NO: 3 or both SEQ ID NO: 2 and SEQ ID NO: 3. In some embodiments, the sample is amplified by polymerase chain reaction (PCR), real-time PCR, reverse transcriptase-PCR, real-time reverse transcriptase-PCR, ligase chain reaction, or transcription-mediated amplification. In some embodiments, the sample is amplified by real-time reverse transcriptase-PCR. In some embodiments, the method further includes sequencing one or more IMP genes in the sample, such as one or more of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75. In some examples, the method includes administering to the subject from whom the sample was obtained a therapeutically effective amount of one or more of tigecycline, colistin, and gentamicin, for example to treat a bacterial infection (such as *Pseudomonas aeruginosa, Klebsiella pneumoniae, Escherichia coli, Enterobacter cloacae, Shigella flexneri, Acinetobacter baumannii, Providencia rettgeri, Achromobacter xylosoxidans,* and *Citrobacter freundii, Serratia marcescens, Proteus mirabilis, Klebsiella oxytoca, Morganella morganii, Providencia stuartii,* or *Enterobacter aerogenes*). In some examples, the bacterial infection is resistant to treatment of carbapenem.

The bla$_{IMP}$ allele detected using the disclosed probes, primers, sets of nucleic acid molecules, and methods, can encode IMP-1, IMP-2, IMP-3, IMP-4, IMP-5, IMP-6, IMP-7, IMP-8, IMP-9, IMP10, IMP-11, MP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, or IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75, or variants thereof. In some examples, the method detects all of these alleles.

The foregoing and other features of the disclosure will become more apparent from the following detailed description of several embodiments which proceeds with reference to the accompanying figures.

SEQUENCE LISTING

Figure 1:
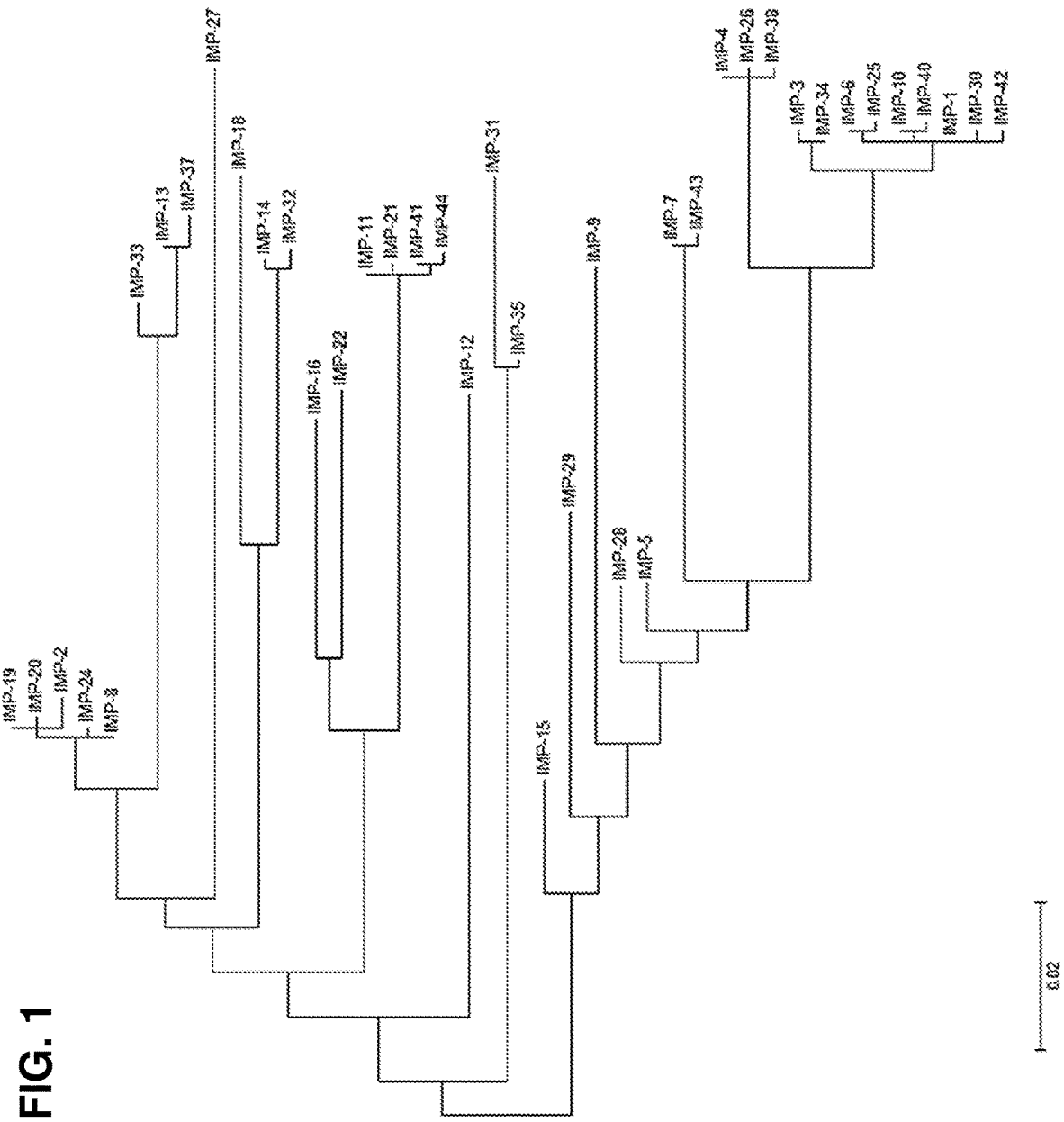
FIG. 1 shows a phylogenetic tree of bla$_{IMP}$ variants.

The nucleic acid sequences are shown using standard letter abbreviations for nucleotide base as defined in 37 C.F.R. 1.822. Only one strand of each nucleic acid sequence is shown, but the complementary strand is understood as included by any reference to the displayed strand. The sequence listing "seq listing.txt" generated on May 16, 2018, 4 kb, filed herewith, is part of the disclosure and is incorporated by reference in it is entirety.

SEQ ID NO: 1 is an IMP forward primer.
SEQ ID NO: 2 is an IMP reverse primer.
SEQ ID NO: 3 is an IMP reverse primer.
SEQ ID NO: 4 is an IMP probe.
SEQ ID NO: 5 is an IMP probe.
SEQ ID NO: 6 is a 16S rRNA forward primer
SEQ ID NO: 7 is a 16S rRNA reverse primer
SEQ ID NO: 8 is a 16S rRNA probe

DETAILED DESCRIPTION OF SEVERAL EMBODIMENTS

I. Overview

The present disclosure provides nucleic acid probes, nucleic acid primers, compositions, kits, and methods for the detection of $bla_{IMP}$ in a sample. The combination of degenerative primers and probes disclosed herein can detect all known IMP variants. The ability of the disclosed methods to detect all known $bla_{IMP}$ variants, rapidly and easily provides for a clinically valuable test useful in prescribing effective antibiotics and identification of harmful bacteria.

Prior phenotypic testing methods to identify carbapenemase-producing isolates can be difficult to interpret, time consuming, and cannot identify specific resistance mechanisms. Currently available testing methods are also limited in the IMP variants they can identify.

The disclosed methods utilize targeted amplification and detectable probes to rapidly detect the presence of $bla_{IMP}$ genes with easy to interpret results, useful in a clinical setting. The disclosed novel compositions, kits, and methods provide a useful and accurate tool that will enhance the surveillance and detection of $bla_{IMP}$ genes.

II. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe." As used herein, the term "comprises" means "includes." Thus, "comprising a probe" means "including a probe" without excluding other elements. It is further to be understood that all base sizes or amino acid sizes, and all molecular weight or molecular mass values, given for nucleic acids or polypeptides are approximate, and are provided for descriptive purposes, unless otherwise indicated.

All publications, patent applications, patents, and other references mentioned herein (including GenBank® Accession numbers available as of Jun. 14, 2017) are incorporated by reference in their entirety. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Administration: To provide or give a subject an agent, such as tigecycline, colistin, or gentamicin by any effective route. Exemplary routes of administration include, but are not limited to, oral, injection (such as subcutaneous, intramuscular, intradermal, intraperitoneal, intravenous), sublingual, rectal, transdermal, intranasal, vaginal, and inhalation routes.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated.

Other examples of in vitro amplification techniques include quantitative real-time PCR; reverse transcriptase PCR; real-time reverse transcriptase PCR (rt RT-PCR or rRT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134); amongst others.

$Bla_{IMP}$: A metallo-β-lactamase gene encoding imipenemase (IMP). The gene was first identified in *Pseudomonas aeruginosa*. $Bla_{IMP}$ has been identified in a number of other bacteria, including, as non-limiting examples *Klebsiella pneumoniae, Escherichia coli, Enterobacter cloacae, Shigella flexneri, Acinetobacter baumannii, Providencia rettgeri, Achromobacter xylosoxidans*, and *Citrobacter freundii, Serratia marcescens, Proteus mirabilis, Klebsiella oxytoca, Morganella morganii, Providencia stuartii*, and *Enterobacter aerogenes*.

The encoded IMP can cleave, and render ineffective, clinically relevant antibiotics (e.g. carbapenems, cephalosporins, and penicillins). $Bla_{IMP}$ genes are generally found on plasmids allowing them to transfer among bacteria. The ease of $Bla_{IMP}$ gene transfer and conferring of antibiotic resistance make the presence of the gene a public health concern.

Carbapenems: A class of antibiotics used in the treatment of infections suspected to be caused by multi-drug resistant (MDR) bacteria. Carbapenems are structurally similar to the penicillins (penams), but the sulfur atom in position 1 of the structure has been replaced with a carbon atom, and an unsaturation has been introduced. The core structure of carbapenems is shown below:

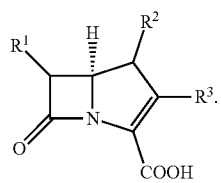

Cephalosporins: A class of β-lactam antibiotics originally derived from the fungus *Acremonium*. First-generation cephalosporins are active predominantly against Gram-positive bacteria, and successive generations have increased activity against Gram-negative bacteria, though sometimes with reduced activity against Gram-positive organisms. The core structure of cephalosporins is shown below:

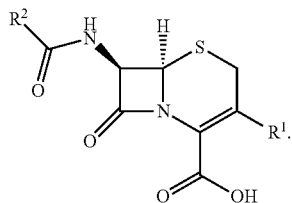

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Contacting: To bring into proximity (e.g. to allow physical contact, for example chemical bonding). In an example, contacting can be in solution (e.g. mixing a primer or probe with a biological or environmental sample). In an example where contacting is between a primer or probe and a sample, hybridization of the probe and primer to a target nucleic acid sequence can occur if the target nucleic acid sequence is present in the sample.

Dark Quencher: A fluorescence quencher that absorbs excitation from a fluorophore and dissipates it as heat, in contrast to re-emit as light of a different wavelength as do typical fluorescence quenchers. Non limiting examples of dark quenchers include IRDye®, IOWA BLACK® quenchers, QXL® quenchers, BLACK HOLE QUENCHER® (BHQ®) dye, and dimethylaminoazobenzenesulfonic acid (Dabcyl). Dark quenchers can be specific for a narrow range of wavelengths or absorb light across the visible spectrum.

Detect: To determine if an agent (such as a signal or particular a particular nucleic acid molecule or protein) is present or absent. In some examples, this can further include quantification. Use of the disclosed probes in particular examples permits detection of a fluorophore, for example detection of a signal from an acceptor fluorophore, which can be used to determine if an IMP is present in a sample.

Detectable Label or Label: An agent capable of detection, for example by spectrophotometry, flow cytometry, or microscopy. For example, a label can be attached to a nucleotide (such as a nucleotide that is part of a probe), thereby permitting detection of the nucleotide, such as detection of the nucleic acid molecule of which the nucleotide is a part or the molecule to which it is hybridized. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Fluorescence Quencher: A molecule suited for a reduction of fluorescence. For example, quenching of a fluorophore's fluorescence occurs when a quencher molecule (such as the fluorescence quenchers disclosed herein) is present in sufficient proximity to the fluorophore that it reduces the fluorescence signal (for example, prior to the binding of a probe to an IMP nucleic acid sequence, when the probe contains a fluorophore and a quencher). In a non-limiting example, fluorescence quenchers are dark quenchers. Exemplary quenchers include TAMRA, BlackBerry Quencher (BBQ), Eclipse Dark Quenchers (EDQ), Deep Dark Quenchers, and Dabcyl.

Fluorophore: A chemical compound, which when excited by exposure to a particular stimulus such as a defined wavelength of light, emits light (fluoresces), for example at a different wavelength (such as a longer wavelength of light). Examples of particular fluorophores that can be used in the probes are disclosed herein.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength that is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Exemplary fluorophores that can be used with the disclosed probes and methods include, but are not limited to, fluorescent proteins (such as GFP, YFP, and the like), xanthene derivatives (e.g., fluorescein (FAM) and 6-hexachloro-fluorescein (HEX)), cyanine derivatives (such as Cy5 and Cy3), squarine derivatines, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In a specific example, the fluorophore attached to a probe (e.g., on the 5'-end of the probe) is FAM, TET, JOE, Yakima Yellow, VIC, HEX, Cy3, Quasar 570, NED, TAMRA, ROX, Texas Red, or Cy5.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid molecule, such as a bacterial nucleic acid molecule. For example, a probe or primer having sufficient identity to a $Bla_{IMP}$ nucleic acid molecule will form a hybridization complex with a $Bla_{IMP}$ nucleic acid molecule.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The probes and primers disclosed herein are capable of hybridizing to $Bla_{IMP}$ nucleic acid molecules.

Imipenemase (IMP): A metallo-β-lactamase (MBL), first identified in Pseudomonas aeruginosa. IMP hydrolyzes a diverse spectrum of substrates including carbapenems, cephalosporins, and penicillins. IMP does not degrade monobactams such as aztreonam and is not inhibited by clavulanic acid and sulbactam. IMP is commonly located on plasmids making it highly mobile and a serious public health concern as it confers resistance to common antibiotics.

IMP is part of a diverse enzyme family that includes 55 IMP variants sharing 80-99.6% amino acid identity. Novel IMP variants are still being discovered. In some examples, IMP variants can vary by one or more single nucleotide polymorphisms (SNPs) from known IMP variants.

IMP variants include IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42, IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75. Furthermore, a newly sequenced variant of IMP-27 is disclosed herein. IMP variants are related as shown in the phylogenetic tree of FIG. 1.

Isolated: An "isolated" biological component (such as a bacterial nucleic acid molecule, whole bacteria, or other biological component) has been substantially separated or purified away from other biological components in which the component naturally occurs, such as other chromosomal and extrachromosomal DNA, RNA, and proteins. Nucleic acid molecules that have been "isolated" include nucleic acid molecules purified by standard purification methods. The term also embraces nucleic acid molecules prepared by recombinant expression in a host cell as well as chemically synthesized nucleic acid molecules, such as probes and primers. Isolated does not require absolute purity, and can include nucleic acid molecules that are at least 50% isolated, such as at least 75%, 80%, 90%, 95%, 98%, 99% or even 100% isolated.

Locked nucleic acid (LNA) analogs: A nucleic acid analog that contains a 2'-O, 4'-C methylene bridge. This bridge-locked in the 3'-endo conformation restricts the flexibility of the ribofuranose ring and locks the structure into a rigid bicyclic formation. LNA-containing oligonucleotides (e.g., probes) have increased thermal stability when hybridized to a complementary DNA or RNA strand. For each incorporated LNA monomer, the melting temperature (Tm) of the duplex can increase by 2-8° C.

Penicillins: A class of antibiotics, used particularly in the treatment of infections caused by staphylococci and streptococci. The core structure of penicillin antibiotics is shown below:

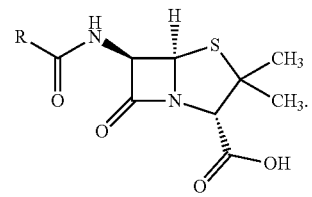

Primers: Short nucleic acid molecules, such as a DNA oligonucleotide, for example sequences of about 15 to 100 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of a bacterial nucleic acid), wherein the sequence of the primer is specific for the target nucleic acid molecule, for example so that the primer will hybridize to the target nucleic acid molecule.

In particular examples, a primer is at least 15 nucleotides in length, such as at least 15 contiguous nucleotides complementary to a target nucleic acid molecule. Particular lengths of primers that can be used in the kits and methods of the present disclosure (for example, to amplify a region of a bacterial nucleic acid) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, 20-40 nucleotides, 15-30 nucleotides, or 17-27 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer3 (world wide web at flypush.imgen.bcm.tmc.edu/primer/primer3_www.cgi).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: An isolated nucleic acid capable of hybridizing to a target nucleic acid (such as a bacterial nucleic acid), which includes a detectable label or reporter molecule attached thereto, such as a covalent attachment. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes (e.g., has attached thereto) at least one fluorophore, such as an acceptor fluorophore or donor fluorophore. In a particular example, a probe includes (e.g., has attached thereto) at least one fluorophore and at least one fluorescence quencher. For example, a fluorophore can be attached at the 5'- or 3'-end of the probe. In specific examples, a fluorophore is attached to the nucleotide at the 5'-end of the probe, the nucleotide at its 3'-end, the phosphate group at its 5'-end or a modified nucleotide, such as a T internal to the probe.

Probes are generally at least 15 nucleotides in length, such as at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 15-60 nucleotides, 15-50 nucleotides, 15-40 nucleotides, 15-40 nucleotides, or 18-30 nucleotides.

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a bacterial nucleic acid) and/or quantitate the initial amounts of a target nucleic acid sequence. In some examples, real time PCR is real time reverse transcriptase PCR (rRT-PCR).

In some examples, the amount of amplified target nucleic acid (such as a bacterial nucleic acid) is detected using a labeled probe, such as a probe labeled with a fluorophore, for example a TAQMAN® probe. In this example, the increase in fluorescence emission is measured in real time, during the course of the RT-PCR. This increase in fluorescence emission is directly related to the increase in target nucleic acid amplification (such as bacterial nucleic acid amplification). In some examples, the change in fluorescence (dRn) is calculated using the equation $dRn=Rn^+ - Rn^-$, with $Rn^+$ being the fluorescence emission of the product at each time point and $Rn^-$ being the fluorescence emission of the baseline. The dRn values are plotted against cycle number, resulting in amplification plots. The threshold value (Ct) is the PCR cycle number at which the fluorescence emission (dRn) exceeds a chosen threshold, which is typically 10 times the standard deviation of the baseline (this threshold level can, however, be changed if desired).

Sample: As used herein, a sample (for example a biological sample or environmental sample) includes all clinical samples useful for detecting antibiotic resistant bacteria (e.g. detection of $Bla_{IMP}$) in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin, and/or embedded in paraffin; autopsy material; tears; milk; skin scrapes; surface washings; urine; sputum; cerebrospinal fluid; prostate fluid; pus; bone marrow aspirates; middle ear fluids; tracheal aspirates (TA); nasopharyngeal aspirates (NA) or swabs (NPS); nasal swabs (NS); nasal washes (NW); throat swabs (TS); dual nasopharyngeal/throat swabs (NPS/TS); lower respiratory tract specimens (including bronchoalveolar lavage (BAL); bronchial wash (BW); sputum; lung tissue); oropharyngeal aspirates or swabs; rectal swabs; vaginal swabs or tissue, or saliva, including specimens from human patients with signs and symptoms of respiratory infection and/or from bacterial culture. Samples also include environmental samples, for example, food, water (such as water from cooling towers, central air conditioning systems, swimming pools, domestic water systems, fountains, or freshwater creeks or ponds), surface swabs (for example, a swab of a counter, bed, floor, wall, or other surface), or other materials that may contain or be contaminated with bacteria containing IMP nucleic acid molecules.

Sequence identity: Sequence identity between two or more nucleic acid or amino acid sequences can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, at least 99%, or at least 99.5% sequence identity to SEQ ID NOS: 1, 2, 3, 4, 5, 6, 7, and 8 are provided herein. One of ordinary skill in the art will appreciate that these sequence identity ranges are provided for guidance only; it is possible that probes and primer can be used that fall outside these ranges.

Subject: A living multi-cellular vertebrate organism, a category that includes human and non-human mammals and primates. In one example the subject is a human. In another example, the subject is a pig. In some examples the subject is a veterinary subject, such as a mouse, rat, rabbit, dog, cat, goat, horse or cow.

TAQMAN® probes: A linear oligonucleotide probe with a 5' reporter fluorophore (for example, 6-carboxyfluorescein (FAM)) and an internal or 3' fluorophore quencher, (for example, BLACK HOLE QUENCHER® 1 (BHQ®1), Iowa Black® FQ quencher, and ZEN™ internal quencher). In the intact TAQMAN® probe, energy is transferred (via FRET) from the short-wavelength fluorophore to the long-wavelength fluorophore, quenching the short-wavelength fluorescence. After hybridization, the probe is susceptible to degradation by the endonuclease activity of a processing Taq polymerase. Upon degradation, FRET is interrupted, increasing the fluorescence from the short-wavelength fluorophore and decreasing fluorescence from the long-wavelength fluorophore.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule, which can include DNA (such as bacterial DNA, or DNA reverse transcribed from bacterial RNA) or RNA (such as bacterial RNA). Purification or isolation of the target nucleic acid molecule, if needed, can be conducted by methods known to those in the art, such as by using a commercially available purification kit or the like. In one example, a target nucleic molecule is a bacterial nucleic acid molecule, such as one or more $Bla_{IMP}$ nucleic acid molecules.

III. Methods of Detecting $Bla_{IMP}$

Methods for the detection of the $Bla_{IMP}$ gene encoding IMP are disclosed. A particular application for the primers and probes disclosed herein is in the detection of any IMP variant. Detection of IMP can be used, for example, to determine prescribing practices (e.g. prescribing of antibiotics not subject to degradation by IMP), and/or to indicate a need for the decontamination of affected surfaces or areas.

The methods described herein can be used for any purpose for which detection of $Bla_{IMP}$ is desirable, including diagnostic and prognostic applications, such as in laboratory and clinical settings. Appropriate samples include any conventional environmental or biological samples, including clinical samples obtained from a human or animal subject (e.g. swine). Suitable samples include blood, derivatives of blood, fractions of blood, serum, extracted galls, biopsied or surgically removed tissue, unfixed tissue, frozen tissue, formalin-fixed tissue, paraffin-embedded tissue, autopsy sample, tears, milk, skin scrapes, surface washings, urine, sputum, cerebrospinal fluid, prostate fluid, pus, bone marrow aspirates, middle ear fluids, tracheal aspirates, nasopharyngeal aspirates or swabs, nasal swabs, nasal washes, throat swabs, dual nasopharyngeal/throat swabs, lower respiratory tract specimens, bronchoalveolar lavage, bronchial wash, sputum, lung tissue, oropharyngeal aspirates or swabs, saliva, vaginal swab, or rectal swab, or bacterial culture. Exemplary environmental samples include, food samples, water samples, and surface swabs (e.g. of a hospital or patient contacted surface). Particularly suitable samples include samples obtained from rectal or environmental swabs. Techniques for acquisition of such samples are described in for example, Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984). This in some examples the method includes obtaining the sample, for example from a human or veterinary subject. In some examples the samples are used directly. In some examples, the samples are concentrated or diluted before analysis. In some examples, nucleic acid molecules (e.g., DNA, RNA, or both) are isolated or purified from the sample and then analyzed using the disclosed methods.

Detecting a $bla_{IMP}$ nucleic acid in a sample includes contacting the sample with at least one $bla_{IMP}$ specific probe disclosed herein that is capable of hybridizing to a $bla_{IMP}$ nucleic acid (such as a nucleic acid probe capable of hybridizing to a $bla_{IMP}$ a nucleic acid, for example a probe including a nucleic acid sequence at least 90%, at least 95%, at least 96%, at least 97%, at least 98%, at least 99%, or 100% sequence identity to SEQ ID NO: 4, a probe including a nucleic acid sequence having at least 90%, at least 95%, at least 96%, at least 97%, at least 98%, at least 99%, or 100% sequence identity to SEQ ID NO: 5, or both probes, and detecting hybridization between the $bla_{IMP}$ nucleic acid and the probe. Detection of hybridization between the probe and the $bla_{IMP}$ nucleic acid indicates the presence of the $bla_{IMP}$ nucleic acid in the sample. In some examples, detection of hybridization between the probe and the $Bla_{IMP}$ nucleic acid in the sample diagnoses bacterial infection with an IMP-containing bacteria in a subject, for example when the sample is a biological sample obtained from the subject, such as a subject suspected of having a bacterial infection.

In some examples, the methods also include contacting the sample with a positive control probe. In some examples, the positive control probe is a probe capable of hybridizing to bacterial 16S rRNA, such as SEQ ID NO: 8 (or a probe having at least 90%, at least 95%, at least 96%, at least 97%, at least 98%, at least 99%, or 100% sequence identity to SEQ ID NO: 8). The probe of SEQ ID NO: 8 can include a detectable label, such as a fluorophore, fluorescence quencher, or both (e.g., fluorophore at 5'-end and quencher at 3'-end).

In some embodiments, bacterial nucleic acids present in a sample are amplified prior to or substantially simultaneously with using one or more hybridization probes for detection. For instance, the bacterial nucleic acid molecules can be amplified, for example to increase the number of nucleic acids that can be detected, thereby increasing the signal obtained. Bla$_{IMP}$ specific nucleic acid primers can be used to amplify a region that is at least about 50, at least about 60, at least about 70, at least about 80 at least about 90, at least about 100, at least about 200, at least about 300, or more base pairs (bp) in length to produce amplified Bla$_{IMP}$ specific nucleic acids. In some embodiments, Bla$_{IMP}$-specific nucleic acid primers can be used to amplify 84 bp and 100 bp Bla$_{IMP}$-specific nucleic acids. Any nucleic acid amplification method can be used to detect the presence of Bla$_{IMP}$ in a sample. In one specific, non-limiting example, polymerase chain reaction (PCR) is used to amplify the bacterial nucleic acid sequences. In other specific, non-limiting examples, real-time PCR, reverse transcriptase-polymerase chain reaction (RT-PCR), real-time reverse transcriptase-polymerase chain reaction (rRT-PCR), ligase chain reaction, or transcription-mediated amplification is used to amplify the bacterial nucleic acid. In a specific example, the bacterial nucleic acid is amplified by rRT-PCR.

Amplification of the bacterial nucleic acid includes contacting the bacterial nucleic acid with one or more primers that are capable of hybridizing to and directing the amplification of an bacterial nucleic acid (such as a nucleic acid capable of hybridizing to a bacterial nucleic acid, for example a primer having at least 90%, at least 95%, at least 96%, at least 97%, at least 98%, at least 99%, or 100% sequence identity to SEQ ID NO: 1, SEQ ID NO: 2, or SEQ ID NO: 3). In some embodiments, the sample is contacted with three primers having at least 90%, at least 95%, at least 96%, at least 97%, at least 98%, at least 99%, or 100% sequence identity to SEQ ID NO: 1, SEQ ID NO: 2 and SEQ ID NO: 3.

In some embodiments, the sample is contacted with at least one pair of primers that include a forward primer (e.g., a primer having at least 90%, at least 95%, at least 96%, at least 97%, at least 98%, at least 99%, or 100% sequence identity to SEQ ID NO: 1), a first reverse primer (e.g., a primer having at least 90%, at least 95%, at least 96%, at least 97%, at least 98%, at least 99%, or 100% sequence identity to SEQ ID NO: 2), and a second reverse primer (e.g., a primer having at least 90%, at least 95%, at least 96%, at least 97%, at least 98%, at least 99%, or 100% sequence identity to SEQ ID NO: 3).

Thus, in some examples, the method includes contacting a nucleic acid-containing sample with (1) a detectably labeled probe having at least 90%, at least 95%, at least 96%, at least 97%, at least 98%, at least 99%, or 100% sequence identity to SEQ ID NO: 4, (2) a detectably labeled probe having at least 90%, at least 95%, at least 96%, at least 97%, at least 98%, at least 99%, or 100% sequence identity to SEQ ID NO: 5, (3) a primer having at least 90%, at least 95%, at least 96%, at least 97%, at least 98%, at least 99%, or 100% sequence identity to SEQ ID NO: 1, (4) a primer having at least 90%, at least 95%, at least 96%, at least 97%, at least 98%, at least 99%, or 100% sequence identity to SEQ ID NO: 2, and (5) a primer having at least 90%, at least 95%, at least 96%, at least 97%, at least 98%, at least 99%, or 100% sequence identity to SEQ ID NO: 3, and incubating the sample with the probes and primers under conditions that allow for amplification and detection of Bla$_{IMP}$ nucleic acid molecules in the sample, for example by detecting hybridization between the detectably labeled probes and a bla$_{IMP}$ allele. In some such examples, each probe includes a fluorophore and a fluorescence quencher.

In some examples, the methods also include amplifying control nucleic acids in the sample (e.g., bacterial 16S rRNA) prior to or substantially simultaneously with using one or more hybridization probes for detecting the control nucleic acids. In some examples, the control primers include SEQ ID NOS: 6 and 7 (or primers having at least 90%, at least 95%, at least 96%, at least 97%, at least 98%, at least 99%, or 100% sequence identity to SEQ ID NO: 6 and 7).

Any type of thermal cycler apparatus can be used for the amplification of the bacterial nucleic acids and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENEAMP® PCR System 9700 (Applied Biosystems; Foster City, Calif.). For real-time PCR, any type of real-time thermocycler apparatus can be used. For example, a BioRad iCycler iQ™, LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), ABI™ system 7500 Fast Dx Real-Time PCR Instrument with SDS software version 1.4 ((Applied Biosystems; Foster City, Calif.), an MX4000™, MX3000™ or MX3005™ (Stratagene; La Jolla, Calif.), and Cepheid SMARTCYCLER™ can be used to amplify nucleic acid sequences in real-time.

In one embodiment, fluorescently-labeled probes rely upon fluorescence resonance energy transfer (FRET), or in a change in the fluorescence emission wavelength of a sample, as a method to detect hybridization of a nucleic acid probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the nucleic acid of interest and in this way, using Bla$_{IMP}$-specific probes, can detect the presence of Bla$_{IMP}$ of any IMP variant in a sample. In one embodiment, fluorescently-labeled DNA probes used to identify amplification products have spectrally distinct emission wavelengths, thus allowing them to be distinguished within the same reaction tube (for example, using multiplex PCR, multiplex RT-PCR or multiplex rRT-PCR).

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid.

In some examples, the methods further include sequencing a Bla$_{IMP}$ nucleic acid detected by the disclosed probe(s) and/or amplified using the disclosed primer(s).

In some examples, the subject from whom the sample was obtained was previously treated with (e.g., administered) a carbapenem, cephalosporin, penicillin or combination thereof. In some examples, such treatment or administration did not successfully treat the bacterial infection.

In some examples, determining that a sample contains IMP bacteria, further includes treating the subject (or other source of the sample) for the IMP bacterial infection, for example by administration or treatment with an antibiotic other than carbapenems, cephalosporins, and penicillins (e.g. treatment with tigecycline, colistin, gentamicin, or combinations thereof). In some embodiments, detection of IMP can result in patient isolation, additional personal protective gear of patient providers, decontamination of affected areas, or additional protocols designed to limit the spread of IMP containing bacteria. Thus in some examples the method is a method of treating an IMP bacterial infection in a subject following detection of Bla$_{IMP}$ nucleic acid in a sample obtained from the subject. In some examples, the method treats an IMP bacterial infection, such as a carbapenem-resistant infection (e.g., carbapenem-resistant Enterobacteriaceae infection), cephalosporin-resistant infection (e.g., cephalosporin-resistant Enterobacteriaceae infection), and/or penicillin-resistant infection (e.g., penicillin-resistant Enterobacteriaceae infection). In some examples, the subject has a carbapenem-resistant Enterobacteriaceae infection (e.g., *Klebsiella* spp. (e.g., *K. pneumoniae* or *K. ozaenae*), *E. coli, Citrobacter freundii, Serratia marcescens, Salmonella* spp., *E. cloacae, S. marcescens, Enterobacter asburiae, Pseudomonas aeruginosa, Enterobacter cloacae, Morganella morganii, Providencia* species (e.g., *Providencia rettegri* or *Providencia stuartii*), or *Enterobacter aerogenes* that includes an IMP). In some examples, the method treats a cephalosporin-resistant infection (e.g., *Neisseria gonorrhoeae, Citrobacter freundii, Enterobacter cloacae, Escherichia coli, Morganella morganii, Proteus vulgaris, Providencia rettgeri, Pseudomonas aeruginosa*, or *Serratia marcescens* that includes an IMP), or a penicillin-resistant infection (e.g., gram negative bacteria, such as *E. coli* or other bacteria listed above, that includes an IMP).

IV. Primers and Probes

Probes and primers for the detection of Bla$_{IMP}$ nucleic acid molecules and suitable for use in the disclosed methods are described herein.

a. Probes

Probes capable of hybridizing to and detecting the presence of Bla$_{IMP}$ nucleic acid molecules are disclosed. The disclosed probes can be between 18 and 30 nucleotides in length, such as 18, 19, 20, 21, 22, 23, 24, 25, 26, 27, 28, 29, or 30 nucleotides in length and are capable of hybridizing to Bla$_{IMP}$ nucleic acids. In embodiments, probes have a melting temperature ($T_m$) of about 55-60° C., such as 55° C., 56° C., 57° C., 58° C., 59° C. or 60° C. In embodiments, the probes have a $T_m$ about 6-12° C. above, about 7-11® C. above, or about 8-10° C. above that of the primers.

The disclosed probes are capable of hybridizing to a Bla$_{IMP}$ nucleic acid molecule, such as those encoding any IMP variant (e.g., IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, IMP-75, as well as variants thereof, such as IMP nucleic acid molecules having at least 80%, at least 85%, at least 90%, at least 95%, at least 96%, at least 97%, at least 98%, or at least 99% sequence identity to any of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75).

In some embodiments, the use of one or more degenerative probes can identify all known IMP variants (e.g., IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75) in a single assay. In embodiments, a probe capable of hybridizing to a Bla$_{IMP}$ nucleic acid molecule is at least 90% identical, such as at least 91%, at least 92%, at least 93%, at least 94%, at least 95%, at least 96%, at least 97%, at least 98%, at least 99%, or even 100% identical to the nucleotide sequence of SEQ ID NO: 4 or SEQ ID NO: 5. In some embodiments, a probe capable of hybridizing to a Bla$_{IMP}$ nucleic acid molecule consists or consists essentially of a nucleic acid sequence of SEQ ID NO: 4 or SEQ ID NO: 5.

The probe can be detectably labeled (e.g., have a labeled attached thereto, such as covalently), either with an isotopic or non-isotopic label, or alternatively the target nucleic acid (such as a Bla$_{IMP}$ nucleic acid) is labeled. Non-isotopic labels can, for instance, include a fluorescent or luminescent molecule, a hapten (for example, biotin), an enzyme or enzyme substrate, or a chemical. Such labels are chosen such that the hybridization of the probe with target nucleic acid (such as a Bla$_{IMP}$ nucleic acid) can be detected. In some examples, the probe is labeled with a fluorophore. Examples of suitable fluorophore labels are given herein. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3' end to prevent extension of the probe by a polymerase.

In particular examples, the acceptor fluorophore (such as a fluorescence quencher) is attached to the 3'-end of the probe and the donor fluorophore is attached to a 5'-end of the probe. In another particular example, the acceptor fluorophore (such as a fluorescence quencher) is attached to a modified nucleotide (such as a T, for example, an internal T) and the donor fluorophore is attached to a 5'-end of the probe. In a particular example, an acceptor fluorophore is a dark quencher, such as Dabcyl, QSY7 (Molecular Probes), QSY33 (Molecular Probes), BLACK HOLE QUENCHER® (BHQ) (Glen Research, Sterling, Va., USA), DEEP DARK QUENCHER™ (Eurogentec), TAMRA™ (Jena Bioscience), BLACKBERRY™ quenchers, ECLIPSE™ Dark Quencher (Glen Research), or IOWA BLACK® FQ (Integrated DNA Technologies, Inc., Coralville, Iowa, USA). In another particular example, the 5' fluorophore is a FAM or HEX fluorophore. In another particular example, BHQ® dye is attached to the 3'-end of the probe.

Additional exemplary fluorophores that can be used in the probes disclosed herein include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red® dye); riboflavin; rosolic acid and terbium chelate derivatives; Cy5.5; Cy56-carboxyfluorescein; boron dipyrromethene difluoride (BODIPY); acridine; stilbene; Cy3® dye; Cy5® dye, VIC® dye; LC Red 640; LC Red 705; and Yakima yellow.

Other suitable fluorophores include those known, for example those available from Molecular Probes (Eugene, Oreg.).

In some embodiments, the probe has the sequence of $AY^e$ TCT $CR^fR^f$ $TCH^g$ $[+A]^aTY^e$ $Y^eCM$ $[+A]^aCR^fT[+A]^aT$ GC (SEQ ID NO: 4). In some embodiments, the probe of SEQ ID NO: 4 is labelled at its 5'-end with an FAM fluorophore and at its 3'-end with a BHQ quencher. In some embodiments, the probe has the sequence TAT $[+G]^aC$ ATC $T[+G]^a$ AAT $[+T]^aA$ $A[+C]^a$ AAA $T[+G]^a$ A (SEQ ID NO: 5). In embodiments, the probe of SEQ ID NO: 5 is labelled at its 5' terminus with a HEX fluorophore and at its 3' terminus with a BHQ® dye. Other suitable fluorophores and fluorophore quenchers can be used. Degenerate probe sequences are listed with the following terms: $a^a[+]$=Locked Nucleic Acid at this position; $^b$ I=Inosine; $^c$M=Mixture of A and C at this position, not necessarily equimolar; $^d$B=Mixture of C, G, and T at this position, not necessarily equimolar; $^e$Y=Mixture of C and T at this position, not necessarily equimolar; $^f$R=Mixture of A and G at this position, not necessarily equimolar; $^g$H=Mixture of A, C, and T at this position, not necessarily equimolar; and $^h$CY5=An alternative fluorophore that can be used at this position is Quasar 670.

b. Primers

Primers capable of hybridizing to and directing the amplification of $Bla_{IMP}$ nucleic acid molecules are disclosed. In embodiments, use of multiple degenerate primers in a single assay allows for the detection of all 55 known IMP variants. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or 40 nucleotides in length. In embodiments, primers have a $T_m$ of about 45-70° C., about 50-65° C., or about 55-60° C.

In some embodiments, a primer is capable of hybridizing to $Bla_{IMP}$ nucleic acid molecule and directing the amplification of the $Bla_{IMP}$ nucleic acid molecule or a portion thereof.

A primer capable of hybridizing to and directing the amplification of a $Bla_{IMP}$ nucleic acid molecule can include a nucleic acid sequence that is at least 90% identical, such as at least 91%, at least 92%, at least 93%, at least 94%, at least 95%, at least 96%, at least 97%, at least 98%, at least 99%, or even 100% identical to the nucleic acid sequence of SEQ ID NO: 1, SEQ ID NO: 2, or SEQ ID NO: 3. In some embodiments, a primer capable of hybridizing to a $Bla_{IMP}$ nucleic acid molecule consists essentially of a nucleic acid sequence of SEQ ID NO: 1, SEQ ID NO: 2, or SEQ ID NO: 3.

In some embodiments, an IMP-Forward (F) primer has the sequence GGC GG[+A]aAT AGA GTG GCT (SEQ ID NO: 1). In some embodiments, an IMP1-Reverse (R) primer has the CCT TAC CGT $HTT$ TTT $I^b$AA GMc A $GB^dT$ CAT (SEQ ID NO: 2). In some embodiments, an IMP2-Reverse (R) primer has the sequence TTT GTA GCT TGC ACC TTA TTG TCT TT (SEQ ID NO: 3). In some embodiments, the primers of SEQ ID NO: 1, SEQ ID NO: 2, and SEQ ID NO: 3 have at least 90%, 91%, 92%, 93%, 94%, 95%, 96%, 97%, 98%, or 99% sequence identity thereto are used in a single assay to detect all known IMP variants. Degenerate primer sequences are listed with the following terms: a $^a[+]$=Locked Nucleic Acid at this position; $^b$ I=Inosine; $^c$M=Mixture of A and C at this position, not necessarily equimolar; $^d$B=Mixture of C, G, and T at this position, not necessarily equimolar; $^e$Y=Mixture of C and T at this position, not necessarily equimolar; $^f$R=Mixture of A and G at this position, not necessarily equimolar; $^g$H=Mixture of A, C, and T at this position, not necessarily equimolar; and $^h$CY5=An alternative fluorophore that can be used at this position is Quasar 670.

c. Controls

In embodiments, the disclosed methods use known primers and probes as an endogenous control, such as those specific for 16S rRNA. An exemplary 16S rRNA-Forward (F) Primer has the sequence: TG GAG CAT GTG GTT TAA TTC GA (SEQ ID NO: 6). An exemplary 16S rRNA-Reverse (R) Primer has the sequence: TG CGG GAC TTA ACC CAACA (SEQ ID NO: 7). An exemplary 16S rRNA-Probe has the sequence CA CGA GCT GAC $AR^fC$ CAT GCA (SEQ ID NO: 8), which in some examples includes a fluorophore at the 5' end (e.g., Cy5® dye) and fluorescence quencher (e.g., BHQ® dye) at the 3' end. Degenerate probe sequences are listed with the following terms: a $^a[+]$=Locked Nucleic Acid at this position; $^b$ I=Inosine; $^c$M=Mixture of A and C at this position, not necessarily equimolar; $^d$B=Mixture of C, G, and T at this position, not necessarily equimolar; $^e$Y=Mixture of C and T at this position, not necessarily equimolar; $^f$R=Mixture of A and G at this position, not necessarily equimolar; $^g$H=Mixture of A, C, and T at this position, not necessarily equimolar; and $^h$CY5=An alternative fluorophore that can be used at this position is Quasar 670.

V. Sets of Nucleic Acid Molecules and Kits

The nucleic acid primers and probes disclosed herein can be supplied in the form of a set of nucleic acid molecules, or a kit, for use in the detection of IMP variants. In such a set or kit, an appropriate amount of one or more of the nucleic acid probes and/or primers can be provided in one or more containers (such as a glass or plastic vial) or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles, which can be made of plastic or glass for example. The sets and kits can include labeled or unlabeled nucleic acid probes for use in detection of IMP variants (such as those disclosed herein). The sets or kits can additionally include one or more control probes and/or primers, for example for the detection of 16S rRNA.

In some embodiments, one or more primers (as described above), such as pairs of primers, may be provided in pre-measured single use amounts in individual, typically disposable, wells, tubes, or equivalent containers. With such an arrangement, the sample to be tested for the presence of $Bla_{IMP}$ nucleic acids can be added to the individual tubes or wells and amplification carried out directly.

The amount of nucleic acid primer supplied in the set or kit can be any appropriate amount, and may depend on the target market to which the product is directed. For instance, if the set or kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A set or kit may include more than two primers, for example three primers, in order to facilitate the PCR amplification of a larger number of IMP variants.

In one example, the set of nucleic acid molecules or kit includes a detectably labeled probe comprising or consisting of SEQ ID NO: 4, a forward primer comprising or consisting of the nucleic acid sequence of SEQ ID NO: 1; and one or more reverse primers comprising or consisting of the nucleic acid sequence of SEQ ID NO: 2, SEQ ID NO: 3, or both SEQ ID NO: 2 and SEQ ID NO: 3. In some examples, the set of nucleic acid molecules or kit further comprises a detectably labeled probe comprising or consisting of the nucleic acid sequence of SEQ ID NO: 5. In some examples, the set of nucleic acid molecules or kit further comprises a forward primer comprising or consisting of the nucleic acid sequence of SEQ ID NO: 6, a reverse primer comprising or consisting of the nucleic acid sequence of SEQ ID NO: 7, a detectably labeled probe comprising or consisting of SEQ ID NO: 8, or combinations thereof. In some examples, each probe in the set or kit is labeled with a radioactive isotope, enzyme substrate, co-factor, ligand, chemiluminescent agent, fluorophore, hapten, enzyme, chemical, fluorescence quencher, or combination thereof. In some examples, each probe in the set or kit is labeled with a fluorophore, a fluorescence quencher, or both.

In some embodiments, kits also may include the reagents necessary to carry out hybridization and/or PCR amplification reactions, such as one or more of DNA sample preparation reagents, polymerase (such as a DNA polymerase, such as Taq® polymerase) appropriate buffers (such as polymerase buffer), salts (for example, magnesium chloride), and deoxyribonucleotides (dNTPs).

Particular embodiments include a kit for detecting $bla_{IMP}$. Such a kit includes at least one probe specific for a $Bla_{IMP}$ nucleic acid (as described above) and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed tubes) or the wells of an array substrate (for example, a 96-well microtiter plate sealed with a protective plastic film). In other particular embodiments, the kit includes equipment, reagents, and instructions for extracting and/or purifying nucleotides from a sample.

In one specific embodiment, the kit includes at least one probe having a nucleic acid sequence at least 90%, at least 95%, at least 96%, at least 97%, at least 98%, at least 99%, or 100% identical to the sequence of SEQ ID NO: 4 and a pair of primers having a nucleic acid sequence at least 90%, at least 95%, at least 96%, at least 97%, at least 98%, at least 99%, or 100% identical to the sequence of SEQ ID NO: 1, 2 and/or 3. In other embodiments, the kit further includes at least one pair of primers including a forward primer having at least 90%, at least 95%, at least 96%, at least 97%, at least 98%, at least 99%, or 100% sequence identity to the sequence of SEQ ID NO: 1 and one or two reverse primers having at least 90%, at least 95%, at least 96%, at least 97%, at least 98%, at least 99%, or 100% sequence identity to the sequence of SEQ ID NO: 2 or SEQ ID NO: 3.

In some examples, the kit includes the probes of SEQ ID NO: 4 and SEQ ID NO: 5, and the primers of SEQ ID NO: 1, SEQ ID NO: 2, and SEQ ID NO: 3. The kit can be designed to detect one or more IMP variants, using the probe and primer sequences provided herein. The kits may additionally include one or more control probes and/or primers, for example for the detection of a 16S rRNA, (such as 1, 2, or 3 of SEQ ID NOs: 6, 7, or 8).

In some examples, the kits may include materials for obtaining, collecting, or storing a sample, such as swabs, lancets, needles, syringes, microscope slides, blood collection tubes, and the like.

V. Imipenemase and $Bla_{IMP}$

The disclosed compositions, kits, and methods can be used to detect $bla_{IMP}$, the gene encoding imipenemase (IMP). The disclosed methods can detect all known IMP variants. IMP is part of a diverse enzyme family of IMP variants sharing about 80-99.6% amino acid identity. IMP variants include IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75. IMP variants are related as shown in the phylogenetic tree of FIG. 1.

Exemplary IMP variants include those listed in Table 1, all reference GenBank® Accession numbers incorporated herein by reference are those sequences were available as of Jun. 14, 2017 and Jun. 13, 2018. A person of ordinary skill in the art could identify additional IMP variants, or IMP variants in a variety of origination bacteria.

TABLE 1

Exemplary IMP variants

| IMP Variant | GenBank® Accession No. Nucleotide Sequence | GenBank® Accession No. Amino Acid Sequence | Originating organism |
| --- | --- | --- | --- |
| IMP-1 | KX987869.1 | APX52851.1 | *Pseudomonas aeruginosa* |
| IMP-2 | KC588963.1 | AGH13135.1 | *Pseudomonas aeruginosa* |
| IMP-3 | NG_049194.1 | WP_063860588.1 | *Shigella flexneri* |
| IMP-4 | AY590475.1 | AAT02662.1 | *Acinetobacter baumannii* |
| IMP-5 | AF290912.1 | AAK27847.1 | *Acinetobacter baumannii* |
| IMP-6 | AB754497.1 | BAM62881.1 | *Providencia rettgeri* |
| IMP-7 | GQ221781.1 | ACT52235.1 | *Pseudomonas aeruginosa* |
| IMP-8 | JQ820406.1 | AFN08667.1 | *Klebsiella pneumoniae* |
| IMP-9 | EU176818.1 | ABX00642.1 | *Pseudomonas aeruginosa* |
| IMP10 | AB074435.1 | BAB72071.1 | *Achromobacter xylosoxidans* |
| IMP-11 | AB074437.1 | BAB72073.1 | *Pseudomonas aeruginosa* |
| IMP-12 | NG_049175.1 | WP_063860574.1 | *Pseudomonas aeruginosa* |
| IMP-13 | NG_049176.1 | WP_042862936.1 | *Pseudomonas aeruginosa* |
| IMP-14 | AY553332.1 | AAT49068.1 | *Pseudomonas aeruginosa* |
| IMP-15 | AY553333.1 | AAT49070.1 | *Pseudomonas aeruginosa* |
| IMP-16 | NG_049179.1 | WP_063860576.1 | *Pseudomonas aeruginosa* |
| IMP-17 | NG_049180.1 | WP_063860577.1 | *Pseudomonas aeruginosa* |
| IMP-18 | AB587676.1 | BAJ19094.1 | *Pseudomonas aeruginosa* |
| IMP-19 | AB184977.1 | BAD34453.1 | *Acinetobacter baumannii* |
| IMP-20 | AB196988.1 | BAD81061.1 | *Pseudomonas aeruginosa* |
| IMP-21 | AB204557.1 | BAD89802.1 | *Pseudomonas aeruginosa* |
| IMP-22 | AB754495.1 | BAM62879.1 | *Providencia rettgeri* |
| IMP-23 | NG_049187.1 | WP_063860582.1 | *Citrobacter freundii* |
| IMP-24 | EF192154.1 | ABM68358.1 | *Serratia marcescens* |
| IMP-25 | EU541448.1 | ACB41775.1 | *Pseudomonas aeruginosa* |
| IMP-26 | ADU04493.1 | HQ685900.1 | *Enterobacter cloacae* |
| IMP-27 | JF894248.1 | AEH41427.1 | *Proteus mirabilis* |
| IMP-28 | JQ407409.1 | AFG73659.1 | *Klebsiella oxytoca* |
| IMP-29 | HQ438058.1 | ADT63777.1 | *Pseudomonas aeruginosa* |
| IMP-30 | NG_049195.1 | WP_063860589.1 | *Pseudomonas aeruginosa* |
| IMP-31 | NG_049196.1 | WP_031943232.1 | *Pseudomonas aeruginosa* |
| IMP-32 | NG_049197.1 | WP_063860590.1 | *Klebsiella pneumoniae* |
| IMP-33 | JN848782.2 | AEU17778.1 | *Pseudomonas aeruginosa* |
| IMP-34 | AB700341.1 | BAM37538.1 | *Klebsiella oxytoca* |
| IMP-35 | NG_049200.1 | WP_063860592.1 | *Pseudomonas aeruginosa* |
| IMP-37 | JX131372.1 | AFP97028.1 | *Pseudomonas aeruginosa* |
| IMP-38 | HQ875573.1 | AEN75249.1 | *Klebsiella pneumoniae* |
| IMP-40 | AB753457.1 | BAM62794.1 | *Pseudomonas aeruginosa* |
| IMP-41 | AB753458.1 | BAM62795.1 | *Pseudomonas aeruginosa* |
| IMP-42 | AB753456.1 | BAM62793.1 | *Acinetobacter soli* |
| IMP-43 | AB777500.1 | BAM98935.1 | *Pseudomonas aeruginosa* |
| IMP-44 | AB777501.1 | BAM98942.1 | *Pseudomonas aeruginosa* |
| IMP-45 | KJ510410.1 | AIA58910.1 | *Pseudomonas aeruginosa* |
| IMP-47 | KP050486.1 | AJO16039.1 | *Serratia marcescens* |
| IMP-48 | KM087857.1 | AIT76110.1 | *Pseudomonas aeruginosa* |
| IMP-49 | KP681694.1 | AK063210.1 | *Pseudomonas aeruginosa* |
| IMP-51 | LC031883.1 | BAQ56016.1 | *Pseudomonas aeruginosa* |
| IMP-52 | LC055762.1 | BAR80870.1 | *Escherichia coli* |
| IMP-53 | NG_049215.1 | WP_063860614.1 | *Pseudomonas aeruginosa* |
| IMP-54 | NG_049216.1 | WP_063860615.1 | *Pseudomonas aeruginosa* |
| IMP-55 | KU299753.1 | ALT07696.1 | *Acinetobacter baumannii* |
| IMP-56 | NG_049218.1 | WP_063860617.1 | *Pseudomonas aeruginosa* |
| IMP-58 | NG_049219.1 | WP_063860618.1 | *Pseudomonas putida* |
| IMP-59 | NG_055477.1 | WP_094009805.1 | *Escherichia coli* |
| IMP-60 | NG_050945.1 | WP_065102288.1 | *Enterobacter cloacae* |
| IMP-61 | NG_051166.1 | WP_065419570.1 | *Acinetobacter baumannii* |
| IMP-62 | NG_051513.1 | WP_069280710.1 | *Pseudomonas aeruginosa* |
| IMP-63 | NG_052049.1 | WP_071593225.1 | *Pseudomonas aeruginosa* |
| IMP-64 | NG_054710.1 | WP_071593226.1 | *Proteus mirabilis* |
| IMP-66 | LC190726.1 | BAV78863.1 | *Escherichia coli* |
| IMP-67 | NG_055271.1 | WP_088245214.1 | *Providencia rettgeri* |
| IMP-68 | NG_055584.1 | WP_096807443.1 | *Klebsiella pneumoniae* |
| IMP-69 | MF678349.1 | ATJ25943.1 | *Providencia sp.* |
| IMP-70 | NG_056176.1 | WP_102607459.1 | *Pseudomonas aeruginosa* |
| IMP-71 | MG818167.1 | AUS29441.1 | *Pseudomonas aeruginosa* |
| IMP-72 | MH021847.1 | AVK78199.1 | *Pseudomonas aeruginosa* |
| IMP-73 | MH021848.1 | AVK78200.1 | *Pseudomonas aeruginosa* |
| IMP-75 | MH243350.1 | AWI33304.1 | *Pseudomonas aeruginosa* |

Novel variants of IMP are continually developing as bacteria undergo mutation and are thus still being identified. These novel variants are modified IMP alleles, often differing by one or several single nucleotide polymorphisms. Examples of the present disclosure assay a novel IMP-27 variant. This variant was detected in an isolate of *Providencia rettgeri*. The novel IMP-27 variant contains a single nucleotide polymorphism at position 661 (G to T) that confers an amino acid change from alanine to serine.

The disclosed primers, probes, kits, and methods can identify one or more bla$_{IMP}$ alleles, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or all 72 of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75. In some examples, the disclosed methods can detect one or more variant bla$_{IMP}$ alleles, such as variants of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or all 72 of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75. In some examples, a variant has at least 80%, at least 85%, at least 90%, at least 95%, at least 96%, at least 97%, at least 98%, at least 99%, or at least 99.5% sequence identity to any of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75.

In some examples, the disclosed methods can detect one or more bla$_{IMP}$ alleles, such as 1, 2, 3, 4, 5, or 6 of IMP-1, IMP-4, IMP-14, IMP-18, IMP-26, and IMP-27. In some examples, the disclosed methods can detect 1, 2, 3, 4, 5, or 6 variants of IMP-1, IMP-4, IMP-14, IMP-18, IMP26- and IMP-27, such as a variant having at least 80%, at least 85%, at least 90%, at least 95%, at least 96%, at least 97%, at least 98%, at least 99%, or at least 99.5% sequence identity to any of IMP-1, IMP-4, IMP-14, IMP-18, IMP-26 and IMP-27.

Additional and/or novel IMP variants can be identified. In some examples, a novel IMP variant is at least 80% identical (such as a nucleic acid sequence at least 81%, 82%, 83%, 84%, 85%, 86%, 87%, 88%, 89%, 90%, 91%, 92%, 93%, 94%, 95%, 96%, 97%, 98%, 99%, or 99.5% identical) to the above listed IMP variants.

In some embodiments, the IMP identified by the compositions and methods of the present disclosure are found in at least *Klebsiella pneumoniae, Escherichia coli, Enterobacter cloacae, Shigella flexneri, Acinetobacter baumannii, Providencia rettgeri, Achromobacter xylosoxidans,* and *Citrobacter freundii, Serratia marcescens, Proteus mirabilis, Klebsiella oxytoca, Morganella morganii, Providencia stuartii,* and *Enterobacter aerogenes*. Bla$_{IMP}$ can be identified in from purified or isolated bacterial DNA, isolated bacteria, or a bacterial culture. In some embodiments, bacteria are cultured in broth or media. In some embodiments, bacterial cultures are started from a swab or sample, for example a biological or environmental swab or sample. Exemplary biological samples include blood, derivatives of blood, fractions of blood, serum, extracted galls, biopsied or surgically removed tissue, unfixed tissue, frozen tissue, formalin-fixed tissue, paraffin-embedded tissue, autopsy sample, tears, milk, skin scrapes, surface washings, urine, sputum, cerebrospinal fluid, prostate fluid, pus, bone marrow aspirates, middle ear fluids, tracheal aspirates, nasopharyngeal aspirates or swabs, nasal swabs, nasal washes, throat swabs, dual nasopharyngeal/throat swabs, lower respiratory tract specimens, bronchoalveolar lavage, bronchial wash, sputum, lung tissue, oropharyngeal aspirates or swabs, saliva, or rectal swab, or bacterial culture. Exemplary environmental samples include food samples, water samples, air samples, soil samples, and surface swabs (e.g. of a hospital or patient contacted surface).

Example 1

Materials and Methods

This example describes materials and methods used for the detection of Bla$_{IMP}$.

DNA Purification.

DNA template for PCR was extracted from bacterial isolates and prepared utilizing heat inactivation and sodium hydroxide as described below.

25 µL of molecular grade water was added to a microcentrifuge tube. Bacterial colonies and 25 µL of 0.1N NaOH were added to the tube. The tubes were heated at 95-99° C. for 10 minutes on heat block. The tubes were then cooled on ice for 3-5 minutes. 18 µL of 0.5M Tris-HCl, pH 8.0 was added. Next 400 µL of cold molecular grade water was added and the tubes centrifuged at 13,200 rpm for 3 minutes and transferred 400 µL of lysate to a new tube.

Real Time Polymerase Chain Reaction (PCR).

Three degenerate oligonucleotide primers (SEQ ID NOS: 1-3) were designed. Primer design is described below with reference to Example 2. PCR reactions were performed with a final volume 20 µL. Reaction contents were as shown in Table. 2.

TABLE 2

| PCR Reaction Mix | |
| --- | --- |
| Qiagen QuantiFast Probe PCR Kit | 1X |
| Primer (SEQ ID NOS: 1-3) | 500 µM of each |
| Probe (SEQ ID NOS: 4-5) | 250 µM of each |
| template DNA | 2 µL |
| Sterile PCR water | To final volume of 20 µL |

PCR cycling parameters were as shown below in Table 3. Reactions were performed in a 7500 Fast Dx Real-Time PCR instrument (Applied Biosystems, Foster City, Calif.).

TABLE 3

PCR conditions

| 1 cycle | 95° C. for 3 minutes |
|---|---|
| 40 cycles | 95° C. for 3 seconds |
|  | 60° C. for 30 seconds* |

*Fluorescence data was collected during the 60° C. incubation step.

Whole Genome Sequencing (WGS).

Isolates that were positively identified by real-time PCR were confirmed by WGS using paired-end reads generated by a MiSeq (Illumina, San Diego, Calif.).

Example 2

Design of Primers and Probes

This example describes the design of primers and probes in the detection of Bla$_{IMP}$.

Primer and probe sequences for real-time PCR are shown in Table 4. Primers were designed to amplify two regions Bla$_{IMP}$ of 84 and 100 bp, respectively. The specificity of each primer was assessed through a BLASTN search. The reference Bla$_{IMP}$ sequences were obtained from NCBI and the sequences aligned using aligned the sequences utilizing MegAlign (DNASTAR®). Primers sequences were manually designed to obtain a T$_m$ (melting temperature) between 55-60° C. When necessary, locked nucleic acid (LNA) bases were used to increase the melting temperature of the primers to 55-60° C. Each primer was designed to be 17-27 bases long, with an optimal length of 18-24 bases. Degenerate primers were designed to ensure detection of all blaIMP variants (degenerate positions covered all possible nucleotide combinations among blaIMP-variants).

Probes were labeled with 6-carboxyfluorescein (FAM) or hexachlorofluorescein (HEX) at the 5'-end. Glycine was avoided at the 5'-end of the probe as it quenches the fluorophore. The 3'-end was labeled with a Black Hole Quencher® (BHQ®) chemical dye (also known as 2,5-Di-(t-butyl)-1,4-hydroquinone). Additional useful labels, combinations of labels, and label positions are known to those of ordinary skill in the art. Probes were designed to be 18-30 bases long with a t$_m$ 8-10° C. above the primers. When necessary, locked nucleic acid bases were utilized to increase the melting temperature to 8-10° C. above the primers. To optimize amplification efficiency and detection of reporter signal, the probes were designed to bind as close as possible to the 3' end of the forward primer. Mismatches between the probe and target sequence were avoided. The degenerate sites of the probes allow for detection of different variants (the degenerate positions covered all possible nucleotide combinations among blaIMP-variants).

TABLE 4

Primers and probes

| Oligo-nucleotide designation | SEQ ID NO: | Nucleotide sequence, 5'-3' |
|---|---|---|
| IMP-Forward (F) Primer | 1 | GGC GG[+A]$^a$AT AGA GTG GCT |
| IMP1-Reverse (R) Primer | 2 | CCT TAC CGT HTT TTT I$^b$AA GM$^c$ A GB$^d$T CAT |
| IMP2-Reverse (R) Primer | 3 | TTT GTA GCT TGC ACC TTA TTG TCT TT |
| IMP1-Probe (FAM) | 4 | FAM-AY$^e$ TCT CR$^f$R$^f$ TCH$^g$ [+A]$^a$TY$^e$ Y$^e$CM [+A]$^a$CR$^f$T[+A]$^a$T GC-BHQ1 |
| IMP2-Probe (HEX) | 5 | HEX-TAT [+G]$^a$C ATC T[+G]$^a$ AAT [+T]$^a$A A[+C]$^a$ AAA T[+G]$^a$ A-BHQ1 |
| 16S rRNA-Forward (F) Primer | 6 | TG GAG CAT GTG GTT TAA TTC GA |
| 16S rRNA-Reverse (R) Primer | 7 | TG CGG GAC TTA ACC CAACA |
| 16S rRNA-Probe (CY5) | 8 | CY5$^h$-CA CGA GCT GAC GAC AR$^f$C CAT GCA-BHQ |

$^a$[+] = Locked Nucleic Acid at this position
$^b$I = Inosine
$^c$M = Mixture of A and C at this position, not necessarily equimolar
$^d$B = Mixture of C, G, and T at this position, not necessarily equimolar
$^e$Y = Mixture of C and T at this position, not necessarily equimolar
$^f$R = Mixture of A and G at this position, not necessarily equimolar
$^g$H = Mixture of A, C, and T at this position, not necessarily equimolar
$^h$CY5 = An alternative fluorophore that can be used at this position is Quasar 670

The IMP2-Reverse primer (SEQ ID NO: 3) and IMP2-probe (SEQ ID NO: 5) were previously described in Zee et al. (BMC Infectious Diseases. 2014, 14:27). The other IMP primers (SEQ ID NO: 1 and 2) and probe (SEQ ID NO: 4) are novel.

Previously established 16S rDNA primers (SEQ ID NO: 6 and 7) and probe (SEQ ID NO: 8) were used as an endogenous control.

Example 3

Detection of bla$_{IMP}$

Figure 2:
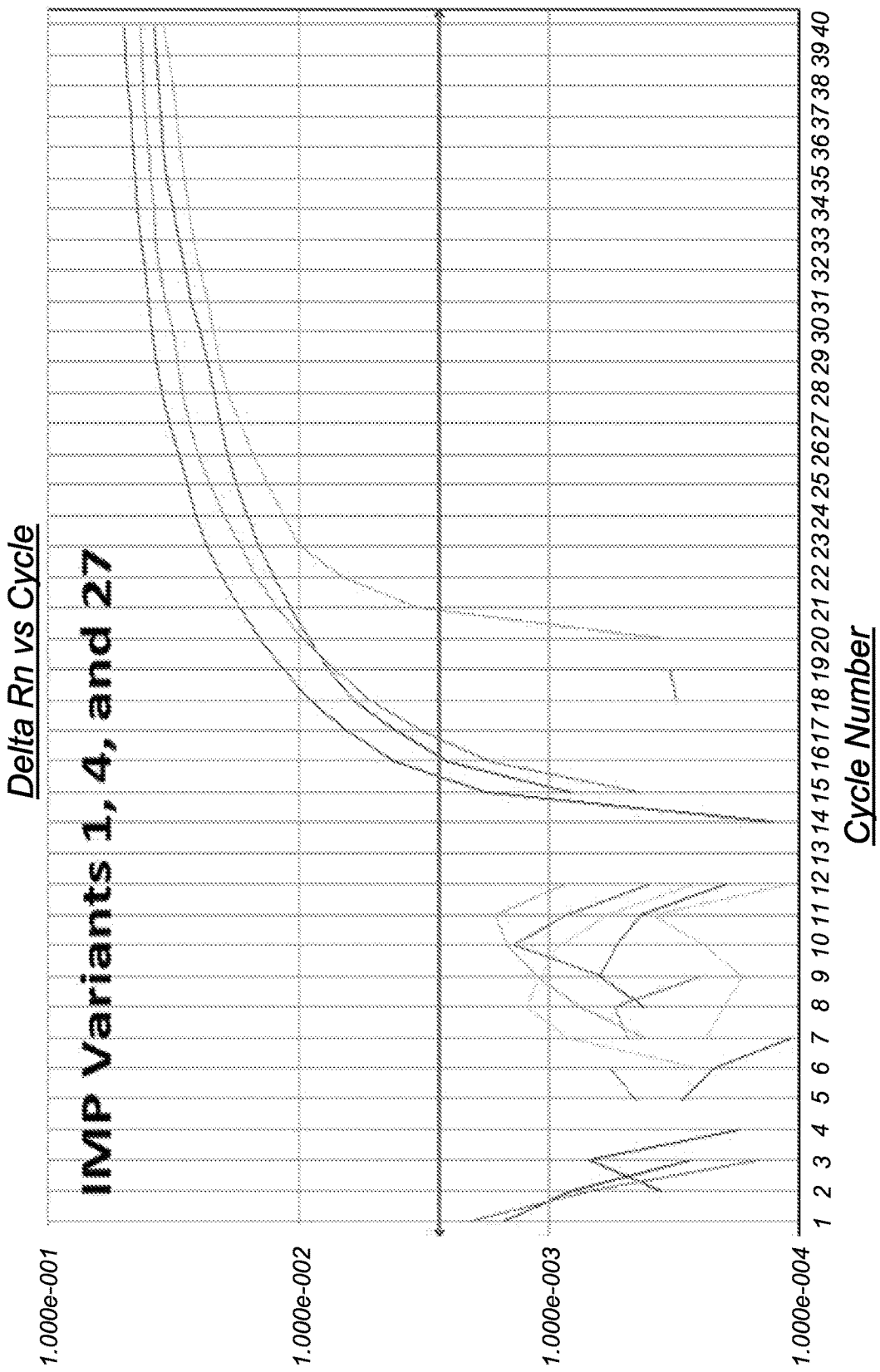
FIG. 2 shows amplification plots of bla$_{IMP}$ positive samples.

This example describes detection of bla$_{IMP}$ by rRT-PCR assay.

rRT-PCR was performed as described in Example 1 using the primers and probes of Example 2 and purified DNA from bacterial isolates of *Pseudomonas aeruginosa, Enterobacter cloacae, Morganella morganii, Providencia species, Providencia rettegri, Klebsiella pneumoniae, Providencia stuartii, Klebsiella pneumoniae*, and *Enterobacter aerogenes*. Each rRT-PCR reaction include three primers (SEQ ID NO: 1, 2, and 3) and two probes (SEQ ID NO: 4 and 5). Probes IMP-P1 and IMP-P2 detected all IMP variants assayed as shown below in Table 5. Example fluorescent counts (CT) are shown in FIG. 2. Thus, the disclosed probes and primers were able to detect multiple variants of IMP as indicated by exponential amplification curves in the real-time PCR assay, whereas a reference strain not containing bla$_{IMP}$ did not show amplification with any of the primers (FIG. 2). In fact, IMP-1, -4, -13, -14, -18 and -27 were all detected, and a variant of IMP-27 that differed by one SNP from the wild type IMP-27 allele was detected.

TABLE 5 blaIMP genes and variants detected by the assay

| ORGANISM | IMP-P1 (CT) | IMP-P2 (CT) | BLA$_{IMP}$ VARIANT CONFIRMED BY WGS |
|---|---|---|---|
| *Pseudomonas aeruginosa* | Undet. | 14.462 | IMP-18 |
| *Enterobacter cloacae* | Undet. | 23.959 | IMP-13 |
| *Enterobacter cloacae* | Undet. | 25.572 | IMP-13 |
| *Morganella morganii* | 20.336 | Undet. | IMP-27 |
| *Providencia* species | 16.819 | Undet. | IMP-27 |
| *Providencia rettegri* | 15.346 | Undet. | IMP-27 variant |
| *Klebsiella pneumoniae* | 14.843 | Undet. | IMP-4 |
| *Providencia stuartii* | 20.91 | Undet. | IMP-27 |
| *Klebsiella pneumoniae* | 16.587 | Undet. | IMP-4 |
| *Klebsiella pneumoniae* | 17.822 | Undet. | IMP-4 |
| *Pseudomonas aeruginosa* | 20.214 | 16.838 | IMP-14 |
| *Enterobacter aerogenes* | 16.653 | Undet. | IMP-4 |
| *Pseudomonas aeruginosa* | 20.063 | Undet. | IMP-1 |
| *Pseudomonas aeruginosa* | Undet. | 14.818 | IMP-18 |
| *Klebsiella pneumoniae* | 18.977 | Undet. | IMP-26 |
| *Providencia* species | 17.647 | Undet. | IMP-27 |

Primers and a probe to 16s rDNA served as a positive control. Detected IMP was confirmed by whole genome sequencing and identified as IMP-18, IMP-13, IMP-26, IMP-27, IMP-27 variant, IMP-4, IMP-14, or IMP-1 as shown in Table 5.

BLAST searches of known IMP sequences indicate the primers and probes disclosed herein can detect all known IMP variants.

These results demonstrate that the disclosed multiplex real-time PCR assay can be used for rapid detection of multiple bla$_{IMP}$ alleles.

Example 4

Multiplex Real-Time PCR for the Detection of bla$_{IMP}$

This example describes a method for detecting bla$_{IMP}$ by multiplex real time PCR.

This method provides instructions for using Applied Biosystems' Fast 7500 Real-Time PCR System (Applied Biosystems, Inc., Foster City, Calif.) to perform TaqMan probe-based real-time PCR detection of blaIMP genes in a single reaction with lysates prepared from Gram-negative bacteria. The 16S rRNA gene, a universal bacterial standard, is utilized as an endogenous control for lysate validation and amplification for each reaction.

This multiplex real-time PCR assay has been shown to detect genes encoding IMP-1, -4, -13, -14, -18, -26, and -27 carried in bacterial isolates. However, based on in silico analysis, the primers and probes described in the current assay should detect all reported blaIMP variants (e.g., any of those provided herein). Novel blaIMP variants may also be detected if modifications in the gene defining the variant do not interfere with association of the PCR primers and probes with their targets. This method can be modified as needed to use with other Real-Time PCR instruments and reagents.

TABLE 6

Acceptance Criteria

| Characteristic | Specification/Expected Performance |
|---|---|
| Sensitivity | 95% |
| Specificity | 95% |
| Accuracy | 95% |
| Precision/Reproducibility | 95% |
| Reference Interval | Not Detected in Wild Type Population |
| Reportable Range for bla$_{IMP}$ target | Positive (Present): When amplification cycle threshold (Ct) is between 10 and 30. Negative (Absent): When amplification cycle threshold (Ct) is greater than 30 or Undetected. |
| Any other performance characteristic required for test performance | Positive (present) endogenous 16S rRNA gene internal control for each sample; 16S CT value is between 10 and 30. This 16S target serves as a control for ensuring that the lysate for each organism has been properly prepared and that the components of the multiplex assay support successful amplification. |

TABLE 7

Sample Summary

| | |
|---|---|
| Total positive samples | 19 |
| Total negative samples | 11 |
| Sample volume (units) | 2 μL |
| Sample matrix | DNA Lysate |

TABLE 8

Qualitative Analysis

| Characteristic | Number of samples | Calculations |
|---|---|---|
| Sensitivity | 19 positive strains will be measured | $\frac{\text{\# correct positive results}}{\text{total \# of positive samples}} \times 100\%$ |
| Specificity | 11 negative strains will be measured | $\frac{\text{\# correct negative results}}{\text{total \# of negative samples}} \times 100\%$ |
| Accuracy | 19 Positive strains + 11 Negative strains will be measured | $\frac{\text{\# of correct results}}{\text{total \# of results}} \times 100\%$ |
| Precision/ Reproducibility | 10 strains comprised of positive and negative samples will be measured in 3 separate runs over at least 2 days by 3 operators | $\frac{\text{\# of results in agreement}}{\text{total \# of results}} \times 100\%$ |

TABLE 9

Origin of Samples

| Validation # | Bank # | Organism | Known Key Resistance | Source | Characterization |
|---|---|---|---|---|---|
| IMP-01 | AR Bank 34 | Klebsiella pneumoniae | IMP-4, TEM-1B, SHV-11 | AR BANK | WGS* |
| IMP-02 | N/A | Klebsiella pneumoniae | IMP-4 | Reference | Sanger Sequencing† |
| IMP-03 | AR Bank 80 | Klebsiella pneumoniae | IMP-4, TEM-1B, OKP-B-2, OXA-1, SFO-1 | AR Bank | WGS* |
| IMP-04 | AR Bank 6 | Escherichia coli | CTX-M-14, TEM-1B, CMY-2 | AR Bank | WGS* |
| IMP-05 | AR Bank 7 | Enterobacter aerogenes | None | AR Bank | WGS* |
| IMP-06 | AR Bank 92 | Pseudomonas aeruginosa | IMP-14, OXA-50, VEB-1, PAO, OXA-10 | AR Bank | WGS* |
| IMP-07 | N/A | Providencia rettgeri | IMP-27 | Reference | WGS* |
| IMP-08 | AR Bank 40 | Klebsiella pneumoniae | VIM-27, CTX-M-15, SHV-11, OXA-1 | AR Bank | WGS* |
| IMP-09 | AR Bank 103 | Pseudomonas aeruginosa | IMP-1, OXA-50, PAO | AR Bank | WGS* |
| IMP-10 | AR Bank 32 | Enterobacter cloacae | KPC-3, TEM-1B, ACT-16 | AR Bank | WGS* |
| IMP-11 | N/A | Providencia stuartii | IMP-27 | Reference | WGS* |
| IMP-12 | N/A | Klebsiella pneumoniae | IMP-4 | Reference | WGS* |
| IMP-13 | N/A | Enterobacter cloacae complex | IMP-13 | Reference | WGS* |
| IMP-14 | AR Bank 161 | Enterobacter aerogenes | IMP-4, TEM-1B, OXA-1, SFO-1 | AR Bank | WGS* |
| IMP-15 | N/A | Klebsiella pneumoniae | IMP-26 | Reference | WGS* |
| IMP-16 | AR Bank 439 | Pseudomonas aeruginosa | IMP-18 | AR Bank | WGS* |
| IMP-17 | N/A | Providencia species | IMP-27 | Reference | WGS* |
| IMP-18 | AR Bank 241 | Pseudomonas aeruginosa | IMP-1, OXA-9, OXA-50, PAO, OXA-101 | AR Bank | WGS* |
| IMP-19 | N/A | Providencia rettgeri | IMP-27 variant | Reference | WGS* |
| IMP-20 | AR Bank 109 | Klebsiella pneumoniae | CTX-M-15, SHV-11, TEM-1B, OXA-1 | AR Bank | WGS* |

TABLE 9-continued

| | | | Origin of Samples | | |
|---|---|---|---|---|---|
| Validation # | Bank # | Organism | Known Key Resistance | Source | Characterization |
| IMP-21 | N/A | Providencia species | IMP-27 | Reference | WGS* |
| IMP-22 | N/A | Pseudomonas aeruginosa | IMP-18 | Reference | WGS* |
| IMP-23 | N/A | Providencia rettgeri | IMP-27 variant | Reference | WGS* |
| IMP-24 | AR Bank 22 | Citrobacter freundii | CMY-84 | AR Bank | WGS* |
| IMP-25 | N/A | Morganella morganii | IMP-27 | Reference | WGS* |
| IMP-26 | AR Bank 138 | Klebsiella pneumoniae | NDM-7, TEM-1B, CTX-M-15, SHV-11 | AR Bank | WGS* |
| IMP-27 | AR Bank 39 | Klebsiella pneumoniae | OXA-181, CTX-M-15, SHV-26 | AR Bank | WGS* |
| IMP-28 | AR Bank 43 | Klebsiella pneumoniae | SHV-12 | AR Bank | WGS* |
| IMP-29 | AR Bank 55 | Escherichia coli | NDM-1, CMY-6, OXA-1 | AR Bank | WGS* |
| IMP-30 | AR Bank 125 | Klebsiella pneumoniae | KPC-3, TEM-IB, OXA-9 | AR Bank | WGS* |
| QC | AR Bank 34 | Klebsiella pneumoniae | IMP-4, TEM-1B, SHV-11 | AR BANK | WGS* |
| QC | AR Bank 92 | Pseudomonas aeruginosa | IMP-14, OXA-50, VEB-1, PAO, OXA-10 | AR Bank | WGS* |
| QC | N/A | Klebsiella pneumoniae | IMP-negative Control | ATCC | ATCC Type Strain |

*CDC Whole genome sequencing (WGS)
†CDC ARCL reference collection confirmed by Sanger sequencing Strains previously characterized by Sanger sequencing, Real-Time PCR and whole genome sequencing will be selected, and assigned a number between IMP #1-30, sub-cultured from frozen stocks, and have DNA lysates prepared. Specimens will be tested in blinded fashion by at least two operators. Reproducibility runs will be conducted in the same blinded fashion by 2-3 operators. Results of each run will be analyzed and validation summarized.

TABLE 10

| Instrumentation | |
|---|---|
| Type | Serial/ID# |
| Applied Biosystems Fast 7500 Real-time PCR System | 275013372 |
| Computer with 7500 Fast System Software v1.4.1 | DXNYWK1 |
| PCR Workstation Hood (Clean Room) | AC648LFUVC-42654 |
| PCR Workstation Hood (Template Room) | AC648LFUVC-43623 |
| Biological Safety Cabinet (optional) | 69953 |
| Centrifuge for 96-well plate (optional) | K1091043 |
| SL-20 micropipette (Clean Room) | F0883048K |
| SL-200 micropipette (Clean Room) | F0882702K |
| PR-1000 micropipette (Clean Room) | F0865904G |
| L-2 XLS (Template Room) | D1228832T |

The disclosed multiplex real-time PCR for the detection of IMP genes is a new method for the qualitative identification of IMP genes, which can be a stand-alone analysis. This multiplex real-time PCR assay has been shown to detect genes encoding IMP-1, -4, -13, -14, -18, -26, and -27 carried in bacterial isolates. However, based on in silico analysis, the assay should detect all reported bla$_{IMP}$ variants. Novel bla$_{IMP}$ variants may also be detected if modifications in the gene defining the variant do not interfere with association of the PCR primers and probes with their targets. The PCR assay's results are not valid if the universal bacterial 16S rRNA endogenous control is not detected in the 16S/IMP reaction well. The results are also not valid if 16S (or the IMP target) is detected at ≤30 Cycle threshold (CT) value in the "No Template Control"; any of these results indicates a failure.

TABLE 11

| Summary of Results | | |
|---|---|---|
| Acceptance Criteria | Met? | Actual Performance |
| Sensitivity | Yes | 100% |
| Specificity | Yes | 100% |
| Accuracy | Yes | 100% (19/19 correct) |
| Precision/Reproducibility | Yes | 100% |
| Reference Interval | Yes | True Positive or True Negative |

TABLE 12

Validation Results

| RT-PCR # | Species | $bla_{IMP}$ Expected Result | 16S Ct Value ($bla_{IMP}$ assay) | $bla_{IMP}$ Probe 1 Ct Value | $bla_{IMP}$ Probe 2 Ct Value | $bla_{IMP}$ Interpretation | Correct |
|---|---|---|---|---|---|---|---|
| IMP-01 | Klebsiella pneumoniae | Positive | 16.331 | 16.794 | Undet. | Positive | True Positive |
| IMP-02 | Klebsiella pneumoniae | Positive | 15.996 | 15.293 | Undet. | Positive | True Positive |
| IMP-03 | Klebsiella pneumoniae | Positive | 16.318 | 16.492 | Undet. | Positive | True Positive |
| IMP-04 | Escherichia coli | Negative | 15.784 | Undet. | Undet. | Negative | True Negative |
| IMP-05 | Enterobacter aerogenes | Negative | 15.835 | Undet. | Undet. | Negative | True Negative |
| IMP-06 | Pseudomonas aeruginosa | Positive | 16.168 | 20.74 | 20.806 | Positive | True Positive |
| IMP-07 | Providencia rettgeri | Positive | 15.849 | 16.409 | Undet. | Positive | True Positive |
| IMP-08 | Klebsiella pneumoniae | Negative | 16.331 | Undet. | Undet. | Negative | True Negative |
| IMP-09 | Pseudomonas aeruginosa | Positive | 16.899 | Undet. | 14.876 | Positive | True Positive |
| IMP-10 | Enterobacter cloacae | Negative | 15.775 | Undet. | Undet. | Negative | True Negative |
| IMP-11 | Providencia stuartii | Positive | 15.783 | 16.669 | Undet. | Positive | True Positive |
| IMP-12 | Klebsiella pneumoniae | Positive | 15.818 | 15.633 | Undet. | Positive | True Positive |
| IMP-13 | Enterobacter cloacae complex | Positive | 15.701 | Undet. | 25.22 | Positive | True Positive |
| IMP-14 | Enterobacter aerogenes | Positive | 15.929 | 15.716 | Undet. | Positive | True Positive |
| IMP-15 | Klebsiella pneumoniae | Positive | 15.788 | 16.678 | Undet. | Positive | True Positive |
| IMP-16 | Pseudomonas aeruginosa | Positive | 17.644 | Undet. | 16.268 | Positive | True Positive |
| IMP-17 | Providencia species | Positive | 16.225 | 15.878 | Undet. | Positive | True Positive |
| IMP-18 | Pseudomonas aeruginosa | Positive | 16.737 | Undet. | 15.548 | Positive | True Positive |
| IMP-19 | Providencia rettgeri | Positive | 16.209 | 16.122 | Undet. | Positive | True Positive |
| IMP-20 | Klebsiella pneumoniae | Negative | 16.298 | Undet. | Undet. | Negative | True Negative |
| IMP-21 | Providencia species | Positive | 16.16 | 15.312 | Undet. | Positive | True Positive |
| IMP-22 | Pseudomonas aeruginosa | Positive | 18.183 | Undet. | 15.66 | Positive | True Positive |
| IMP-23 | Providencia rettgeri | Positive | 16.407 | 15.712 | Undet. | Positive | True Positive |
| IMP-24 | Citrobacter freundi | Negative | 15.935 | Undet. | Undet. | Negative | True Negative |
| IMP-25 | Morganella morganii | Positive | 16.42 | 15.438 | Undet. | Positive | True Positive |
| IMP-26 | Klebsiella pneumoniae | Negative | 16.124 | Undet. | Undet. | Negative | True Negative |
| IMP-27 | Klebsiella pneumoniae | Negative | 16.209 | Undet. | Undet. | Negative | True Negative |
| IMP-28 | Klebsiella pneumoniae | Negative | 16.326 | Undet. | Undet. | Negative | True Negative |
| IMP-29 | Escherichia coli | Negative | 15.985 | Undet. | Undet. | Negative | True Negative |
| IMP-30 | Klebsiella pneumoniae | Negative | 16.398 | Undet. | Undet. | Negative | True Negative |
| QC | Klebsiella pneumoniae | Positive | 16.248 | 16.725 | Undet. | Positive | True Positive |
| QC | Pseudomonas aeruginosa | Positive | 16.385 | 20.13 | 17.895 | Positive | True Positive |
| QC | Klebsiella pneumoniae | Negative | 15.938 | Undet. | Undet. | Negative | True Negative |
| QC | Klebsiella pneumoniae | Positive | 16.45 | 16.261 | Undet. | Positive | True Positive |

TABLE 12-continued

Validation Results

| RT-PCR # | Species | $bla_{IMP}$ Expected Result | 16S Ct Value ($bla_{IMP}$ assay) | $bla_{IMP}$ Probe 1 Ct Value | $bla_{IMP}$ Probe 2 Ct Value | $bla_{IMP}$ Interpretation | Correct |
|---|---|---|---|---|---|---|---|
| QC | Pseudomonas aeruginosa | Positive | 16.705 | 18.706 | 19.697 | Positive | True Positive |
| QC | Klebsiella pneumoniae | Negative | 16.094 | Undet. | Undet. | Negative | True Negative |

TABLE 13

Table 13: Reproducibility Results

| RT-PCR # | Species | $bla_{IMP}$ Expected Results | 16S Ct Value ($bla_{IMP}$ assay) | $bla_{IMP}$ Probe 1 Ct Value | $bla_{IMP}$ Probe 2 Ct Value | $bla_{IMP}$ Interpretation | Correct |
|---|---|---|---|---|---|---|---|
| IMP-02 | Klebsiella pneumoniae | Positive | 16.124 | 15.6 | Undet. | Positive | True Positive |
| IMP-02 | Klebsiella pneumoniae | Positive | 16.156 | 15.121 | Undet. | Positive | True Positive |
| IMP-02 | Klebsiella pneumoniae | Positive | 17.017 | 15.056 | Undet. | Positive | True Positive |
| IMP-06 | Pseudomonas aeruginosa | Positive | 16.17 | 19.775 | 17.836 | Positive | True Positive |
| IMP-06 | Pseudomonas aeruginosa | Positive | 16.239 | 19.365 | 19.538 | Positive | True Positive |
| IMP-06 | Pseudomonas aeruginosa | Positive | 16.805 | 23.157 | 18.657 | Positive | True Positive |
| IMP-13 | Enterobacter cloacae | Positive | 15.708 | Undet | 19.077 | Positive | True Positive |
| IMP-13 | Enterobacter cloacae | Positive | 15.805 | Undet. | 25.654 | Positive | True Positive |
| IMP-13 | Enterobacter cloacae | Positive | 16.39 | Undet. | 22.67 | Positive | True Positive |
| IMP-15 | Klebsiella pneumoniae | Positive | 15.706 | 16.639 | Undet | Positive | True Positive |
| IMP-15 | Klebsiella pneumoniae | Positive | 15.776 | 16.447 | Undet. | Positive | True Positive |
| IMP-15 | Klebsiella pneumoniae | Positive | 16.349 | 16.155 | Undet. | Positive | True Positive |
| IMP-16 | Pseudomonas aeruginosa | Positive | 17.152 | Undet | 14.749 | Positive | True Positive |
| IMP-16 | Pseudomonas aeruginosa | Positive | 17.582 | Undet. | 16.01 | Positive | True Positive |
| IMP-16 | Pseudomonas aeruginosa | Positive | 18.295 | Undet. | 15.19 | Positive | True Positive |
| IMP-05 | Enterobacter aerogenes | Negative | 15.776 | Undet | Undet | Negative | True Negative |
| IMP-05 | Enterobacter aerogenes | Negative | 15.791 | Undet. | Undet. | Negative | True Negative |
| IMP-05 | Enterobacter aerogenes | Negative | 16.309 | Undet. | Undet. | Negative | True Negative |
| IMP-10 | Enterobacter cloacae | Negative | 15.755 | Undet | Undet | Negative | True Negative |
| IMP-10 | Enterobacter cloacae | Negative | 15.684 | Undet. | Undet. | Negative | True Negative |
| IMP-10 | Enterobacter cloacae | Negative | 16.28 | Undet. | Undet. | Negative | True Negative |
| IMP-20 | Klebsiella pneumoniae | Negative | 16.468 | Undet | Undet | Negative | True Negative |
| IMP-20 | Klebsiella pneumoniae | Negative | 16.23 | Undet. | Undet. | Negative | True Negative |
| IMP-20 | Klebsiella pneumoniae | Negative | 16.775 | Undet. | Undet. | Negative | True Negative |
| IMP-28 | Klebsiella pneumoniae | Negative | 16.115 | Undet | Undet | Negative | True Negative |
| IMP-28 | Klebsiella pneumoniae | Negative | 16.02 | Undet. | Undet. | Negative | True Negative |
| IMP-28 | Klebsiella pneumoniae | Negative | 16.484 | Undet. | Undet. | Negative | True Negative |
| IMP-29 | Escherichia coli | Negative | 15.733 | Undet | Undet | Negative | True Negative |

TABLE 13-continued

Table 13: Reproducibility Results

| RT-PCR # | Species | bla$_{IMP}$ Expected Results | 16S Ct Value (bla$_{IMP}$ assay) | bla$_{IMP}$ Probe 1 Ct Value | bla$_{IMP}$ Probe 2 Ct Value | bla$_{IMP}$ Interpretation | Correct |
|---|---|---|---|---|---|---|---|
| IMP-29 | Escherichia coli | Negative | 15.729 | Undet. | Undet. | Negative | True Negative |
| IMP-29 | Escherichia coli | Negative | 16.234 | Undet. | Undet. | Negative | True Negative |
| QC | Klebsiella pneumoniae | Positive | 16.248 | 16.725 | Undet. | Positive | True Positive |
| QC | Klebsiella pneumoniae | Positive | 16.253 | 16.448 | Undet. | Positive | True Positive |
| QC | Klebsiella pneumoniae | Positive | 16.62 | 15.684 | Undet. | Positive | True Positive |
| QC | Pseudomonas aeruginosa | Positive | 16.385 | 20.13 | 17.895 | Positive | True Positive |
| QC | Pseudomonas aeruginosa | Positive | 16.453 | 20.399 | 19.727 | Positive | True Positive |
| QC | Pseudomonas aeruginosa | Positive | 16.811 | 20.822 | 18.669 | Positive | True Positive |
| QC | Klebsiella pneumoniae | Negative | 15.938 | Undet. | Undet. | Negative | True Negative |
| QC | Klebsiella pneumoniae | Negative | 15.875 | Undet. | Undet. | Negative | True Negative |
| QC | Klebsiella pneumoniae | Negative | 16.388 | Undet. | Undet. | Negative | True Negative |

TABLE 14

Samples and Reference Materials

| Material | Characterization |
|---|---|
| QuantiFast Probe PCR Kit* (#204254 for 400 reactions) or equivalent PCR Kit* (Qiagen) | Enzyme, dNTP, buffer mix, and low ROX dye for fast and efficient DNA synthesis in fast format real-time PCR assays. (Optimized for use on Applied Biosystems 7500 Fast Instrument) |
| Master P Mix** containing: IMP forward (F) and IMP reverse (R) primer 1, IMP reverse (R) primer 2; IMP labeled probe 1** (5' FAM, and 3' BHQ1) and IMP labeled probe 2** (5'HEX, and 3'BHQ1); 16S rRNA forward (F) and reverse (R) primers & labeled probe** (5' Cy5, and 3' BHQ) (see Table 4) | Working stock diluted from CDC-BCF containing primers and probes for target genes to be detected (IMP1 Forward primer, reverse primer, and probe, IMP2 Forward primer, reverse primer, and probe multiplexed with 16S forward primer, reverse primer and probe for endogenous control) |
| Sterile reagent grade type I H2O (Promega) | Certified DNA/RNA-Nuclease-Free Water suitable for molecular applications. |
| Lysate (Molecular Grade Water; 1N NaOH; 1M Tris HCl pH 8.0) | Crude lysate prepared via heated 0.1N NaOH lysis, followed by neutralization with 0.5M Tris HCL pH 8.0, and brought to volume with molecular grade water. |

*QuantiFast Probe PCR Kit stored at −15° C. to −30° C. upon arrival. Once kits are thawed for use, they are stored at 2-8° C. for up to 2 months.
**Light-sensitive reagents; keep shielded from light with aluminum foil.

In view of the many possible embodiments to which the principles of the disclosure may be applied, it should be recognized that illustrated embodiments are only examples of the disclosure and should not be considered a limitation on the scope of the invention. Rather, the scope of the invention is defined by the following claims. We therefore claim as our invention all that comes within the scope and spirit of these claims.

We claim:

1. An isolated mixture of degenerate probes comprising or consisting of the nucleic acid sequence of SEQ ID NO: 4 and at least one attached detectable label.

2. The isolated mixture of degenerate probes of claim 1, wherein the at least one attached detectable label comprises a radioactive isotope, enzyme substrate, co-factor, ligand, chemiluminescent agent, fluorophore, hapten, enzyme, chemical, fluorescence quencher, or combination thereof.

3. An isolated primer consisting of the nucleic acid sequence of SEQ ID NO: 1 or an isolated mixture of degenerate primers comprising or consisting of the nucleic acid sequence of SEQ ID NO: 2.

4. A method for detecting a bla$_{IMP}$ allele in a sample, comprising:
   contacting the sample with a mixture comprising (1) detectably labeled degenerate nucleic acid probes comprising or consisting of the nucleic acid sequence of SEQ ID NO: 4, or (2) detectably labeled degenerate nucleic acid probes comprising or consisting of the nucleic acid sequence of SEQ ID NO: 4 and a detectably labeled nucleic acid probe comprising or consisting of the nucleic acid sequence of SEQ ID NO: 5; and
   detecting hybridization between the detectably labeled probes and the bla$_{IMP}$ allele, wherein detection of hybridization indicates a bla$_{IMP}$ allele is present in the sample.

5. The method of claim 4, wherein the bla$_{IMP}$ allele encodes an imipenemase (IMP).

6. The method of claim 5, wherein the IMP is one or more of IMP-1, IMP-2, IMP-3, IMP-4, IMP-5, IMP-6, IMP-7, IMP-8, IMP-9, IMP10, IMP-11, IMP-12, IMP-13, IMP-14, IMP-15, IMP-16, IMP-18, IMP-19, IMP-20, IMP-21, IMP-22, IMP-24, IMP-25, IMP-26, IMP-27, IMP-28, IMP-29, IMP-30, IMP-31, IMP-32, IMP-33, IMP-34, IMP-35, IMP-37, IMP-38, IMP-40, IMP-41, IMP-42 IMP-43, IMP-44, IMP-45, IMP-46, IMP-47, IMP-48, IMP-49, IMP-50, IMP-51, IMP-52, IMP-53, IMP-54, IMP-55, IMP-56, IMP-58, IMP-59, IMP-60, IMP-61, IMP-62, IMP-63, IMP-64, IMP-66, IMP-67, IMP-68, IMP-69, IMP-70, IMP-71, IMP-72, IMP-73, and IMP-75 and variants thereof.

7. The method of claim 6, wherein the IMP is one or more of IMP-1, IMP-4, IMP-26 IMP-14, IMP-18, IMP-27, and variants thereof.

8. The method of claim 4, wherein the one or more detectably labeled degenerate probes comprising or consisting of the nucleic acid sequence of SEQ ID NO: 4 are each labeled with a radioactive isotope, enzyme substrate, co-factor, ligand, chemiluminescent agent, fluorophore, hapten, enzyme, chemical, fluorescence quencher, or combination thereof.

9. The method of claim 4, wherein the sample comprises an isolated bacterium.

10. The method of claim 4, wherein the sample is a biological sample from a subject known or suspected of having a bacterial infection.

11. The method of claim 4, wherein the sample:
    comprises blood, derivatives of blood, fractions of blood, serum, extracted galls, biopsied or surgically removed tissue, unfixed tissue, frozen tissue, formalin-fixed tissue, paraffin-embedded tissue, autopsy sample, tears, milk, skin scrapes, surface washings, urine, sputum, cerebrospinal fluid, prostate fluid, pus, bone marrow aspirates, middle ear fluids, tracheal aspirates, nasopharyngeal aspirates or swabs, nasal swabs, nasal washes, throat swabs, dual nasopharyngeal/throat swabs, lower respiratory tract specimens, bronchoalveolar lavage, bronchial wash, sputum, lung tissue, oropharyngeal aspirates or swabs, saliva, or rectal swab, or bacterial culture, or
comprises an environmental or food sample suspected of bacterial contamination.

12. The method of claim 4, further comprising amplifying nucleic acid molecules in the sample with a forward primer comprising or consisting of the nucleic acid sequence of SEQ NO: 1 and a reverse primer comprising or consisting of the nucleic acid sequence of SEQ ID NO: 2, SEQ ID NO: 3 or both SEQ ID NO: 2 and SEQ ID NO: 3.

13. The method of claim 12, wherein the nucleic acid molecules in the sample are amplified by polymerase chain reaction (PCR), real-time PCR, reverse transcriptase-PCR, real-time reverse transcriptase-PCR, ligase chain reaction, or transcription-mediated amplification.

14. The method of claim 4, further comprising administering a therapeutically effective amount of tigecycline, colistin, gentamicin, or combinations thereof to a subject from whom the sample was obtained.

15. A set of nucleic acid molecules, comprising:
the mixture of degenerate probes of claim 1,
a forward primer comprising or consisting of the nucleic acid sequence of SEQ ID NO: 1; and
one or more reverse primers comprising or consisting of the nucleic acid sequence of SEQ ID NO: 2, SEQ ID NO: 3, or both SEQ ID NO: 2 and SEQ ID NO: 3.

16. The set of nucleic acid molecules according to claim 15, further comprising:
a detectably labeled probe comprising or consisting of the nucleic acid sequence of SEQ ID NO: 5.

17. The set of nucleic acid molecules according to claim 15, further comprising:
a forward primer comprising or consisting of the nucleic acid sequence of SEQ ID NO: 6;
a reverse primer comprising or consisting of the nucleic acid sequence of SEQ ID NO: 7;
a detectably labeled degenerate probe comprising or consisting of SEQ ID NO: 8, or combinations thereof.

18. The set of nucleic acid molecules according to claim 15, wherein each probe is labeled with a radioactive isotope, enzyme substrate, co-factor, ligand, chemiluminescent agent, fluorophore, hapten, enzyme, chemical, fluorescence quencher, or combination thereof.

19. The set of nucleic acid molecules of claim 15, wherein each probe in the set is labeled with a fluorophore.

20. A kit for detecting a $bla_{IMP}$ allele in a sample, comprising:
the set of nucleic acid molecules of claim 17; and
one or more of a polymerase, dNTPs, and $MgCl_2$.

* * * * *